US007022717B2

(12) United States Patent
Bridger et al.

(10) Patent No.: US 7,022,717 B2
(45) Date of Patent: Apr. 4, 2006

(54) CHEMOKINE RECEPTOR BINDING HETEROCYCLIC COMPOUNDS

(75) Inventors: Gary James Bridger, Bellingham, WA (US); Eva Maria Boehringer, White Rock (CA); Zhongren Wang, Langley (CA); Dominique Schols, Herent (BE); Renato Tony Skerlj, Vancouver (CA); David Earl Bogucki, Surrey (CA)

(73) Assignee: AnorMED, Inc., Langley (CA)

( * ) Notice: Subject to any disclaimer, the term of this patent is extended or adjusted under 35 U.S.C. 154(b) by 75 days.

(21) Appl. No.: 10/703,781

(22) Filed: Nov. 7, 2003

(65) Prior Publication Data
US 2004/0102428 A1    May 27, 2004

Related U.S. Application Data

(63) Continuation of application No. 09/740,050, filed on Dec. 15, 2000, now Pat. No. 6,667,320.

(60) Provisional application No. 60/172,153, filed on Dec. 17, 1999.

(51) Int. Cl.
*A61P 9/10*   (2006.01)
*A61K 31/44*   (2006.01)
*C07D 245/00*   (2006.01)
*C07D 255/00*   (2006.01)

(52) U.S. Cl. .................. 514/336; 514/340; 514/342; 540/460; 540/467; 540/474

(58) Field of Classification Search ................ 514/336, 514/340, 342; 540/460, 467, 474
See application file for complete search history.

(56) References Cited

U.S. PATENT DOCUMENTS

| 5,021,409 A | 6/1991 | Murrer et al. ............. 514/183 |
| 5,583,131 A | 12/1996 | Bridger et al. ............. 514/183 |
| 5,698,546 A | 12/1997 | Bridger et al. ............. 514/183 |
| 5,817,807 A | 10/1998 | Bridger et al. ............. 540/474 |
| 6,365,583 B1 | 4/2002 | MacFarland et al. ....... 514/183 |

FOREIGN PATENT DOCUMENTS

| EP | 0 434 385 | 6/1991 |
| EP | 0 747 368 | 12/1996 |
| WO | WO 92/16494 | 10/1992 |
| WO | WO 93/12096 | 6/1993 |
| WO | WO 95/18808 | 7/1995 |
| WO | WO 00/02870 | 1/2000 |
| WO | WO 00/45814 | 8/2000 |

OTHER PUBLICATIONS

International Search Report based on International Application No. PCT/CA99/00619.

Arenburg et al., "The Role of CXC Chemokines in the Regulation of Angiogenesis in Non-small Cell Lung Cancer", J. Leukocyte Biol. 62(5):554-562 (1997).
Bleul et al., "The Lymphocyte Chemoattractant SDF-1 is a Ligand for LESTR/Fusin and Blocks HIV-1 Entry", NATURE, 382(6594): 829-832 (1996).
Boshoff et al., "Angiogenic and HIV-Inhibitory Functions of KSHV-Encoded Chemokines", SCIENCE, 278(5336):290-294 (1997).
Bridger et al., "Synthesis and Structure-Activity Relationships of Phenylenebis (methylene)-Linked Bis-Tetraazamacrocyles That Inhibit HIV Replication. Effects of Macrocyclic Ring Size and Substituents on the Aromatic Linker", J. Med. Chem. 38:366-378 (1995).
Bridger et al., "Synthesis amd Structure-Activity Relationships of Phenylenebis (methylene)-Linked Bis-Tetraazamacrocyles That Inhibit HIV Replication. 2. Effect of Heteroaromatic Linkers on the Activity of Bicyclams", J. Med. Chem., 39(1):109-119 (1996).
Carroll et al. "Differential Regulation of HIV-1 Fusion Cofactor Expression by CD28 Costimulation of $CD4^+T$ Cells", SCIENCE, 276(5310):273-276 (1997).
Chemical Abstracts, 113:40649 (1990).
Chemical Abstracts, 111:190197 (1987).
Chemical Abstracts, 123:56538 (1994).
De Clercq et al., "Highly Potent and Selective Inhibition of Human Immunodeficiency Virus by the Byclam Derivative JM3100", Antimicrobial Agents & Chemotherapy, 38(4): 668-674 (1994).
Donzella et al., "AMD3100, A Small Molecule Inhibitor of HIV-1 Entry Via the CXCR4 Co-Receptor", Nature Medicine, 4(1):72-77 (1998).
Fukuyama et al., "2- and 4-Nitrobenzenesulfonamides: Exceptionally Versatile Means for Preparation of Secondary Amines and Protection of Amines", Tetrahedron Letters, 36(36):6373-74 (1995).
Gupta et al., "Chemokine Receptors in Human Endothelial Cells", J. Biological Chem., 273(7):4282-87 (1998).

(Continued)

*Primary Examiner*—Brenda Coleman
(74) *Attorney, Agent, or Firm*—Morrison & Foerster LLP

(57) ABSTRACT

The present invention is drawn to novel antiviral compounds, pharmaceutical compositions and their use. More specifically this invention is drawn to derivatives of monocyclic polyamines which have activity in standard tests against HIV- or FIV-infected cells as well as other biological activity related to binding of ligands to chemokine receptors that mediate a number of mammalian embryonic developmental processes.

11 Claims, 2 Drawing Sheets

OTHER PUBLICATIONS

Hoxie et al., "*CD4-Independent Infection by HIV-2 is Mediated by Fusin/CXCR4*", CELL, 87:745-756 (1996).

Joao et al. "*Quantitative Structural Activity Relationship Study of Bis-Tetraazacyclic Compounds. A Novel Series of HIV-1 and HIV-2 Inhibitors*", J. Med. Chem. 38:3865-73 (1995).

Leff, "*Besides Aiding AIDS Entry, Receptor Honchos Fetal Growth of Brain, Gut, Blood Systems*", Bioworld Today, 9:111 (1998).

Miedema et al., "*Changing Virus-Host Interactions in the Course of HIV-1 Infection*", Immunological Reviews, 140: 35-72 (1994).

Morphy et al., "*Towards Tumour Targeting with Copper-Radiolabelled Macrocycle-Antibody Conjugates: Synthesis, Antibody Linkage, and Complexation Behaviour*", J. Chem. Soc. Perkin Trans., 2:573-85 (1990).

Oberlin et al., "*The CXC Chemokine SDF-1 is the Ligand for LESTR/Fusin and Prevents Infection by T-Cell-Line-Adapted HIV-1*", NATURE, 382:833-835 (1996).

Ponath et al., "*Chemokine Receptor Antagonists: Novel Therapeutics for Inflammation and AIDS*", Exp. Opin. Invest. Drugs, 7:1-18 (1998).

Schols et al., "*Inhibition of T-Tropic HIV Strains by Selective Antagonization of the Chemokine Receptor CXCR4*", J. Exp. Med., 186(8):1383-88 (1997).

Schols et al., "*Bycyclams, A Class of Potent Anti-HIV Agents, are Targeted at the HIV Coreceptor Fusin/CXCR-4*", Antiviral Research, 35:147-156 (1997).

Tachibana et al., "*The Chemokine Receptor CXCR4 is Essential for Vascularization of the Gastrointestinal Tract*", NATURE, 393:591-94 (1998).

Wyatt et al., "*The HIV-1 Envelope Glycoproteins: Fusogens, Antigens, and Immunogens*", SCIENCE, 280:1884-88 (1998).

Zou et al., "*Function of the Chemokine Receptor CXCR4 in Haematopoiesis and In Cerebellar Development*", NATURE, 393:595-99 (1998).

Figure 1 AMD 8897
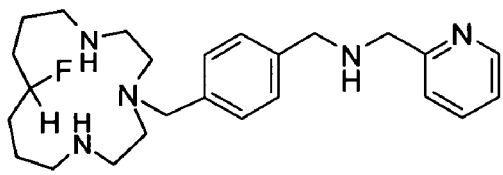
Figure 2 AMD 8880
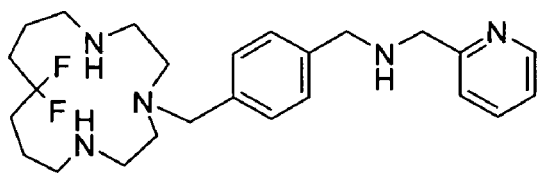
Figure 3 AMD 8748
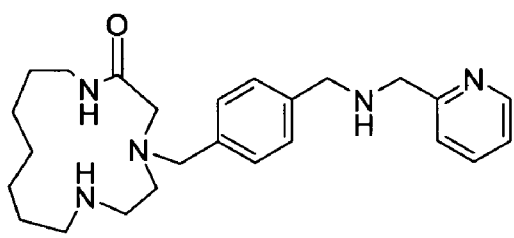
Figure 4 AMD 8922
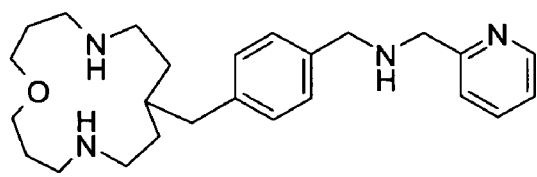
Figure 5 AMD 8779
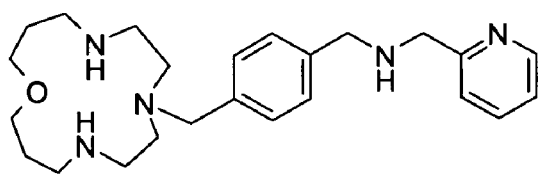

Figure 6 AMD 8834
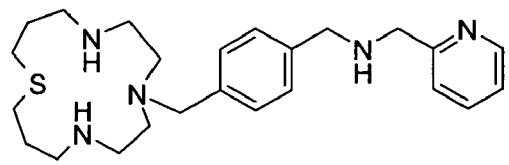
Figure 7 AMD 9424
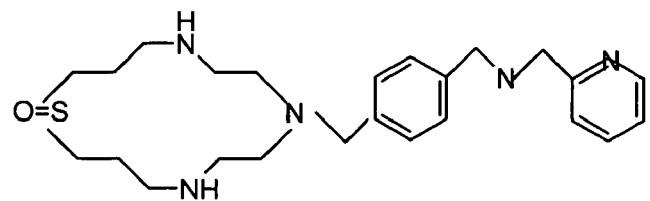
Figure 8 AMD 9408
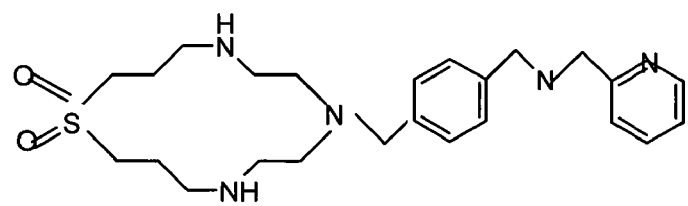
Figure 9 AMD -Exp 40
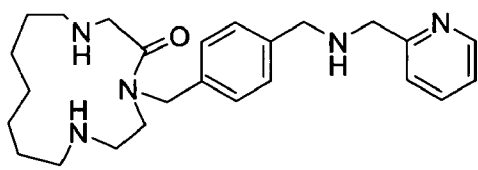
Figure 10 AMD 3100
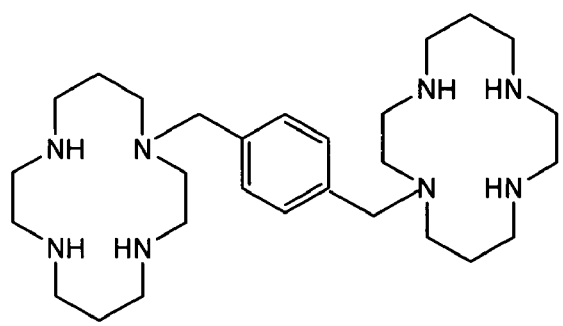

CHEMOKINE RECEPTOR BINDING HETEROCYCLIC COMPOUNDS

CROSS-REFERENCE TO RELATED APPLICATION

This application is a continuation of U.S. Ser. No. 09/740,050 filed 15 Dec. 2000 now U.S. Pat. No. 6,667,320 which claims priority under 35 U.S.C. § 119(e) to application Ser. No. 60/172,153 filed 17 Dec. 1999. The contents of these applications are incorporated herein by reference.

TECHNICAL FIELD

This invention generally relates to novel compounds, pharmaceutical compositions and their use. This invention more specifically relates to novel heterocyclic compounds that bind to chemokine receptors, including CXCR4 and CCR5, and demonstrate protective effects against infection of target cells by a human immunodeficiency virus (HIV).

BACKGROUND OF THE INVENTION

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs* 7:1–18 (1998); Baggiolini, M., *Nature* 392:565–568 (1998); Locati, et al., *Annu. Rev. Med.* 50:425–40 (1999)). These chemotactic cytokines, or chemokines, constitute a family of proteins, approximately 8–10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR" while those of the α-chemokines are designated "CXCR."

Chemokines are considered to be principal mediators in the initiation and maintenance of inflammation (see *Chemokines in Disease* published by Humana Press (1999), Edited by C. Herbert; Murdoch, et al., *Blood* 95:3032–3043 (2000)). More specifically, chemokines have been found to play an important role in the regulation of endothelial cell function, including proliferation, migration and differentiation during angiogenesis and re-endothelialization after injury (Gupta, et al., *J. Biol. Chem.* 7:4282–4287 (1998); Volin, et al., *Biochem. Biophys Res. Commun.* 242:46–53 (1998)). Two specific chemokines have been implicated in the etiology of infection by human immunodeficiency virus (HIV).

In most instances, HIV initially binds via its gp120 envelope protein to the CD4 receptor of the target cell. A conformational change appears to take place in gp120 which results in its subsequent binding to a chemokine receptor, such as CCR5 (Wyatt, et al., *Science* 280:1884–1888 (1998); Rizzuto, et al., *Science* 280:1949–1953 (1998); Berger, et al., *Annu. Rev. Immunol.* 17:657–700 (1999)). HIV-1 isolates arising subsequently in the infection bind to the CXCR4 chemokine receptor.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll, et al., *Science* 276:273–276 (1997); Feng et al., *Science* 272: 872–877 (1996); Bleul, et al., *Nature* 382:829–833 (1996); Oberlin, et al., *Nature* 382:833–835 (1996); Cocchi, et al., *Science* 270:1811–1815 (1995); Dragic, et al., *Nature* 381: 667–673 (1996); Deng, et al., *Nature* 381:661–666 (1996); Alkhatib, et al., *Science* 272:1955–1958, (1996)). During the course of infection within a patient, it appears that a majority of HIV particles shift from the M-tropic to the more pathogenic T-tropic viral phenotype (Blaak, et al., *Proc. Natl. Acad. Sci.* 97:1269–1274 (2000); Miedema, et al., *Immune. Rev.* 140:35 (1994); Simmonds, et al., *J. Virol.* 70:8355–8360 (1996); Tersmette, et al., *J. Virol.* 62:2026–2032, (1988); Connor, R. I., Ho, D. D., *J. Virol.* 68:4400–4408 (1994); Schuitemaker, et al., *J. Virol.* 66:1354–1360 (1992)). The M-tropic viral phenotype correlates with the virus's ability to enter the cell following binding of the CCR5 receptor, while the T-tropic viral phenotype correlates with viral entry into the cell following binding and membrane fusion with the CXCR4 receptor. Clinical observations suggest that patients who possess genetic mutations in CCR5 appear resistant, or less susceptible to HIV infection (Liu, et al., *Cell* 86:367–377 (1996); Samson, et al., *Nature* 382:722–725 (1996); Michael, et al., *Nature Med.* 3:338–340 (1997); Michael, et al., *J. Virol.* 72:6040–6047 (1998); Obrien, et al., *Lancet* 349:1219 (1997); Zhang, et al., *AIDS Res. Hum. Retroviruses* 13:1357–1366 (1997); Rana, et al., *J. Virol.* 71:3219–3227 (1997); Theodorou, et al., *Lancet* 349:1219–1220 (1997). Despite the number of chemokine receptors which have been reported to HIV mediate entry into cells, CCR5 and CXCR4 appear to be the only physiologically relevant coreceptors used by a wide variety of primary clinical HIV-1 strains (Zhang, et al., *J. Virol.* 72:9307–9312 (1998); Zhang, et al., *J. Virol.* 73:3443–3448 (1999); Simmonds, et al., *J. Virol.* 72:8453–8457 (1988)). Fusion and entry of T-tropic viruses that use CXCR4 are inhibited by the natural CXC-chemokine stromal cell-derived factor-1, whereas fusion and entry of M-tropic viruses that use CCR5 are inhibited by the natural CC-chemokines namely, Regulated on Activation Normal T-cell Expressed and Secreted (RANTES) and Macrophage Inflammatory proteins (MIP-1 alpha and beta).

In addition to serving as a co-factor for HIV entry, the direct interaction of virus-associated gp120 with CXCR4 has been recently suggested as a possible cause of CD8$^+$ T-cell apoptosis and AIDS-related dementia via induction of neuronal cell apoptosis (Hesselgesser, et al., *Curr. Biol.* 8:595–598 (1998); Hesselgesser, et al., *Curr. Biol.* 7:112–121 (1997); Hesselgesser, et al., "Chemokines and Chemokine receptors in the Brain" in Chemokines in Disease published by Humana Press (1999), Edited by C. Herbert; Herbein, et al., *Nature* 395:189–194 (1998); Buttini, et al., *Nature Med.* 4:441–446 (1998); Ohagen, et al., *J. Virol.* 73:897–906 (1999); Biard-Piechaczyk, et al., *Virology* 268:329–344 (2000); Sanders, et al., *J. Neuroscience Res.* 59:671–679 (2000); Bajetto, et al., *J. Neurochem.* 73:2348–2357 (1999); Zheng, et al., *J. Virol.* 73:8256–8267 (1999)).

However, the binding of chemokine receptors to their natural ligands appears to serve a more evolutionary and central role than only as mediators of HIV infection. The binding of the natural ligand, pre-B-cell growth-stimulating factor/stromal cell derived factor (PBSF/SDF-1) to the CXCR4 chemokine receptor provides an important signaling mechanism: CXCR4 or SDF-1 knock-out mice exhibit cerebellar, cardiac and gastrointestinal tract abnormalities and die in utero (Zou, et al., *Nature* 393:591–594 (1998); Tachibana, et al., *Nature* 393:591–594 (1998); Nagasawa, et al., *Nature* 382:635–638 (1996)). CXCR4-deficient mice also display hematopoietic defects (Nagasawa, et al., *Nature* 382:635–638 (1996)); the migration of CXCR4 expressing leukocytes and hematopoietic progenitors to SDF-1 appears to be important for maintaining B-cell lineage and localization of CD34$^+$ progenitor cells in bone marrow (Bleul, et al., *J. Exp. Med.* 187:753–762 (1998); Viardot, et al., *Ann. Hematol.* 77:195–197 (1998); Auiti, et al., *J. Exp. Med.* 185:111–120 (1997); Peled, et al., *Science* 283:845–848 (1999); Qing, et al., *Immunity* 10:463–471 (1999); Lataillade, et al., *Blood* 95:756–768 (1999); Ishii, et al., *J. Immunol.* 163:3612–3620 (1999); Maekawa, et al., *Internal Medicine* 39:90–100 (2000); Fedyk, et al., *J. Leukocyte Biol.* 66:667–673 (1999); Peled, et al., *Blood* 95:3289–3296 (2000)).

The signal provided by SDF-1 on binding to CXCR4 may also play an important role in tumor cell proliferation and regulation of angiogenesis associated with tumor growth (See "*Chemokines and Cancer*" published by Humana Press (1999); Edited by B. J. Rollins; Arenburg, et al., *J. Leukocyte Biol.* 62:554–562 (1997); Moore, et al., *J. Invest. Med.* 46:113–120 (1998); Moore, et al., *Trends cardiovasc. Med.* 8:51–58 (1998); Seghal, et,al., *J. Surg. Oncol.* 69:99–104 (1998)); the known angiogenic growth factors VEG-F and bFGF, up-regulate levels of CXCR4 in endothelial cells, and SDF-1 can induce neovascularization in vivo (Salcedo, et al., *Am. J. Pathol.* 154:1125–1135 (1999)); Leukemia cells that express CXCR4 migrate and adhere to lymph nodes and bone marrow stromal cells that express SDF-1 (Burger, et al., *Blood* 94:3658–3667 (1999); Arai, et al., *Eur. J. Haematol.* 64:323–332 (2000); Bradstock, et al., *Leukemia* 14:882–888 (2000); Burger et al., *Blood* 96:265502663 (2000); Mörle, R. et al. *Brit. J. Haematol.* 110:561–582 (2000).

The binding of SDF-1 to CXCR4 has also been implicated in the pathogenesis of atherosclerosis (Abi-Younes, et al., *Circ. Res.* 86:131–138 (2000)), renal allograft rejection (Eitner, et al., *Transplantation* 66:1551–1557 (1998)), asthma and allergic airway inflammation (Yssel, et al., *Clinical and Experimental Allergy* 28:104–109 (1998); Nagase, et al., *J. Immunol.* 164:5935–5943 (2000); Gonzalo, et al., *J. Immunol.* 165:499–508 (2000)), Alzheimer's disease (Xia, et al., *J. Neurovirology* 5:32–41 (1999)) and arthritis (Nanki, et al., *J. Immunol.* 164:5010–5014 (2000)).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols, et al., *J. Exp. Med.* 186:1383–1388 (1997); Schols, et al., *Antiviral Research* 35:147–156 (1997); Bridger, et al., *J. Med. Chem.* 42:3971–3981 (1999); Bridger, et al., "Bicyclam Derivatives as HIV Inhibitors" in *Advances in Antiviral Drug Design* Volume 3, p161–229; Published by JAI press (1999); Edited by E. De Clercq). Small molecules, such as bicyclams, appear to specifically bind to CXCR4 and not CCR5 (Donzella, et al., *Nature Medicine* 4:72–77 (1998)). These experiments demonstrated interference with HIV entry and membrane fusion into the target cell in vitro. More recently, bicyclams were also shown to inhibit fusion and replication of Feline Immunodeficiency Virus (FIV) that uses CXCR4 for entry (Egberink, et al., *J. Virol.* 73:6346–6352 (1999)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco, et al., *Antimicrobial Agents and Chemother.* 44:51–56 (2000)).

U.S. Pat. No. 5,583,131, U.S. Pat. No. 5,698,546, U.S. Pat. No. 5,817,807, U.S. Pat. No. 5,021,409 and U.S. Pat. No. 6,001,826, which are incorporated herein by reference, disclose cyclic compounds that are active against HIV-1 and HIV-2 in in vitro tests. It was subsequently disclosed, in published PCT application PCT/CA99/00619 (WO 00/029870), incorporated herein by reference, that these compounds as well as additional compounds with less complex structures exhibit anti-HIV activity by binding to the chemokine receptor CXCR4 and/or CCR5 expressed on the surface of certain cells of the immune system. This competitive binding protects these target cells, which utilize the CXCR4 receptor for entry from infection by HIV. In addition, the compounds antagonize the binding, signaling and chemotactic effects of the natural ligand for CXCR4, i.e., the chemokine stromal cell-derived factor 1α (SDF-1), and also have protective effects against HIV infection of target cells by binding in vitro to the CCR5 receptor.

Additionally, published PCT application PCT/CA00/00104, (WO 00/45814), incorporated herein by reference, discloses that the cyclic polyamine antiviral agents described in the above-mentioned documents have the effect of enhancing production of white blood cells as well as exhibiting antiviral properties. Thus, these agents are useful for controlling the side-effects of chemotherapy, enhancing the success of bone marrow transplantation, enhancing wound healing and bum treatment, as well as combating bacterial infections in leukemia.

Published PCT application PCT/CA00/00321 (WO 00/56729), incorporated herein by reference, discloses additional heterocyclic compounds that exhibit anti-HIV activity by binding to the chemokine receptors CXCR4 and CCR5 expressed on the surface of certain cells of the immune system. This competitive binding thereby protects these target cells, which utilize the CXCR4 or CCR5 receptors for entry, from infection by HIV. In addition, these compounds antagonize the binding, signaling and chemotactic effects of the natural ligand for CXCR4, i.e., the chemokine stromal cell-derived factor 1α (SDF-1) and/or the natural ligand for CCR5, the chemokine RANTES.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

The present invention describes novel compounds that exhibit protective effects against HIV infection of target cells by binding to the chemokine receptors CXCR4 or CCR5, in a similar manner to the previously disclosed macrocyclic compounds, and that are additionally useful in other indications addressed by the compounds as described above.

DISCLOSURE OF THE INVENTION

The present invention provides novel compounds that bind chemokine receptors and interfere with the binding of the natural ligand thereto, and are useful as agents demonstrating protective effects on target cells from HIV infection. The invention compounds act as antagonists or agonists of chemokine receptors and exhibit biological activities related to the ability of these compounds to inhibit the binding of chemokines to their receptors.

Accordingly, the present invention provides a compound of Formula 1

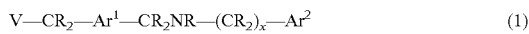

(1)

including the pharmaceutically acceptable salts and protected forms thereof, wherein V is a substituted heterocycle of 9–24 members containing 2–4 optionally substituted amine nitrogen atoms spaced from each other by 2 or more optionally substituted carbon atoms, and which heterocycle may optionally comprise a fused aromatic or heteroaromatic ring, and wherein (a) said heterocycle contains at least one O or S, said O or S spaced from any adjacent heteroatom by at least 2 carbon atoms, and wherein said S is optionally oxidized or (b) at least one carbon atom in said ring is substituted by an electron-withdrawing substituent, or (c) both (a) and (b);

and wherein each R is independently H or a straight chain, branched or cyclic alkyl containing 1–6C;

x is 0–4;

$Ar^1$ is an unsubstituted or substituted aromatic or heteroaromatic moiety; and $Ar^2$ is an unsubstituted or substituted aromatic or heterocyclic group.

Other aspects of the invention are directed to the pharmaceutical compositions comprising a therapeutically effective amount of the compound of Formula 1 and to methods of treating a condition of the human body or the bodies of other mammals comprising the administration of a pharmaceutical or veterinary composition which contains a therapeutically effective amount of the compound of Formula 1. In other aspects, the invention is directed to a method for blocking or interfering with the binding of a chemokine receptor with its natural ligand, by contacting the chemokine receptor with an effective amount of the compound of Formula 1.

In still other aspects, the invention includes the use of a compound of Formula 1 in the manufacture of a medicament for the treatment of a disease in which blocking or interfering with binding of a chemokine receptor with its natural ligand is advantageous and for protecting target cells possessing chemokine receptors, the binding to which by a pathogenic agent results in disease or pathology. The invention is also directed to methods of treatment as outlined above.

BRIEF DECRIPTION OF THE DRAWINGS

FIG. 1, shows the structural formula of compound AMD 8897.

FIG. 2, shows the structural formula of compound AMD 8880.

FIG. 3, shows the structural formula of compound AMD 8748.

FIG. 4, shows the structural formula of compound AMD 8922.

FIG. 5, shows the structural formula of compound AMD 8779.

FIG. 6, shows the structural formula of compound AMD 8834.

FIG. 7, shows the structural formula of compound AMD 9424.

FIG. 8, shows the structural formula of compound AMD 9408.

FIG. 9, shows the structural formula of compound AMD-Exp 40.

FIG. 10, shows the structural formula of compound AMD 3100.

DETAILED DESCRIPTION OF THE INVENTION

The present invention is directed to compounds of Formula 1 which can act as agents that modulate chemokine receptor activity. Such chemokine receptors include but are not limited to CCR1, CCR2, CCR3, CCR4, CCR5, CCR6, CCR7, CCR8 and CXCR1, CXCR2, CXCR3, CXCR4 and CXCR5.

The compounds of Formula 1 that demonstrate protective effects on target cells from HIV infection so as to bind specifically to the chemokine receptor, affect the binding of a natural ligand or chemokine to a receptor such as CXCR4 and/or CCR5. They are also useful as agents which affect chemokine receptors, such as CCR1, CCR2, CCR3, CCR4, CCR5, CCR6, CCR7, CCR8 and CXCR1, CXCR2, CXCR3, CXCR4 and CXCR5 where such chemokine receptors have been correlated as being important mediators of many human inflammatory as well as immunoregulatory diseases. Thus, the compounds of Formula 1, which modulate the activity of such chemokine receptors are useful for the treatment or prevention of such diseases.

The term "modulators" as used herein encompasses antagonist, agonist, partial antagonist, and or partial agonist, inhibitors, and activators. In a preferred embodiment of the present invention, compounds of Formula 1 demonstrate protective effects against HIV infection by inhibiting binding of HIV to a chemokine receptor, such as CXCR4 and/or CCR5 of a target cell.

The compounds of Formula 1 that inhibit chemokine receptors may be used for the treatment of diseases associated with hematopoiesis, including but not limited to, controlling the side-effects of chemotherapy, enhancing the success of bone marrow transplantation, enhancing wound healing and burn treatment, as well as combating bacterial infections and leukemia.

These compounds of Formula 1 are thus also useful for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, asthma, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myasteria gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria, vasculitis (e.g., necrotizing, cutaneous, and hypersensitivity vasculitis); eosinphilic myotis, eosiniphilic fasciitis; and cancers.

The compounds of the invention that activate or promote chemokine receptor function may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which cause immunosuppression; immunosuppression due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinphilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, *Herpesvirus saimiri*, and Kaposi's sarcoma herpesvirus, also known as human herpesvirus 8, and poxvirus *Moluscum contagiosum.*

Compounds of Formula 1 may be used in combination with any other pharmaceutical composition where such combined therapy may be useful to modulate chemokine receptor activity and thereby prevent and treat inflammatory and immunoregulatory diseases, including, for example, in combinations with one or more agents useful in the prevention or treatment of HIV. Examples of such agents include:

(1) nucleotide reverse transcriptase inhibitor such as zidovudine, didanosine, lamivudine, zalcitabine, abacavir, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, etc.; and (3) protease inhibitors such as saquinavir, ritonavir, indinavir, nelfinavir, amprenavir, palinavir, lasinavir, Kaletra™ (lopinavir/ritonavir), etc.

Such combinations the compounds of the present invention and other HIV agents may be administered separately or in conjunction; the administration of one element may be prior to, concurrent to, or subsequent to the administration of other agent(s).

The compounds of Formula 1 may be administered by oral, parenteral (e.g., intramuscular, intraperitoneal, intravenous, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The compounds of Formula 1 may be used to treat animals, including mice, rats, horses, cattle, sheep, dogs, cats, and monkey, and are also effective for use in humans.

The compounds of the invention may be supplied as "pro-drugs," or, protected forms of the compounds of Formula 1, which release the compound after administration to a patient. For example, the compound may carry protective groups which are split off by hydrolysis in body fluids, e.g., in the bloodstream, thus releasing active compound or is oxidized or reduced in body fluids to release the compound. A discussion of pro-drugs may be found in Smith and Williams' *Introduction to the Principles of Drug Design*, H. J. Smith, Wright, Second Edition, London 1988.

Acid addition salts, which are pharmaceutically acceptable, such as salt with inorganic base, a salt with organic base, a salt with inorganic acid, a salt with organic acid, a salt with basic or acidic amino acid, etc. and non-toxic metal complexes are also encompassed in the present invention. Examples of a salt with an inorganic base include a salt with alkali metal (e.g. sodium, potassium, etc.), alkaline earth metal (e.g. calcium, magnesium, etc.), aluminum, ammonium, etc. Examples of the salt with an organic base include a salt with trimethylamine, triethylamine, pyridine, picoline, ethanolamine, diethanolamine, triethanolamine, dicyclohexylamine, N,N'-dibenzylethylenediamine etc. Examples of the salt with an inorganic acid include a salt with hydrochloric acid, hydrobromic acid, nitric acid, sulfuric acid, phosphoric acid, etc. Examples of the salt with an organic acid include a salt with formic acid, oxalic acid, acetic acid, tartaric acid, methanesulfonic acid, benzenesulfonic acid, malic acid, methanesulfonic acid, benzenesulfonic acid, p-toluenesulfonic acid, etc. Examples of salts with basic amino acids include a salt with arginine, lysine, ornithine, etc. Examples of salts with the acidic amino acid include a salt with aspartic acid, glutamic acid, etc. Non-toxic in the present tense has to be considered with reference to the prognosis for the infected subject without treatment. Copper and zinc complexes are preferred although other metals such as nickel, cobalt or rhubidium, may be used.

The compounds of Formula 1 may form hydrates or solvates. Some compounds of Formula 1 exist as regioisomers, configurational isomers, conformers, diastereoisomeric forms and mixtures of diastereoisomeric forms thereof; it is possible to isolate individual isomers using known separation and purification methods, if desired. The invention includes mixtures of these stereoisomers as well as isolated forms. The mixtures may contain the stereoisomers in any ratio. Compounds of the invention also include racemates, which can be separated into the (S)-compounds and (R)-compounds by optical resolution; individual optical isomers and mixtures thereof are included in the scope of the present invention.

The compounds of Formula 1 may be administered alone or as an admixture with a pharmaceutically acceptable carrier (e.g. solid formulations such as tablets, capsules, granules, powders, etc.; liquid formulations such as syrups, injections, etc.) may be orally or non-orally administered. Examples of non-oral formulations include injections, drops, suppositories and pessaryies.

In the above Formula 1, V contains 2–4 N, preferably 3–4 N if there is no additional heteroatom. Preferable ring sizes for V are 9–18 members, more preferably 12–16 members. V may also include a fused aromatic or heteroaromatic ring, preferably 1,2 or 1,3 or 1,4 phenylene or 2,6 or 2,5 or 2,4 or 2,3 pyridinylene. The fused ring may also be, for example, 2,5 or 2,6 pyrimidinylene or 2,4 or 2,3 pyrrolylene.

In the above Formula 1, the required electron withdrawing substituents present at at least one C in ring V may be halogen, nitro, cyano, carboxylic acid, a carboxylic ester with an alcohol of 1–6C or amide formed from an amine of 0–12C, a sulfonic or sulfinic acid or a sulfonic or sulfinic ester or amide, $CF_3$, and the like. A preferred electron withdrawing substituent is $=O$, as well as halo.

Examples of halogen include fluorine, chlorine, bromine, iodine, etc., with fluorine and chlorine preferred.

In the above Formula 1, $Ar^2$ is an optionally substituted heterocyclic group or aromatic group. Examples of aromatic groups include benzene and naphthalene, or dihydronaphthalene and tetrahydronaphthalene. Examples of heterocyclic groups include 5 to 6-membered saturated, partially saturated, or aromatic heterocyclic rings containing 1 to 4 heteroatoms selected from nitrogen, oxygen and sulfur. The heterocycles may be pyridine, quinoline, isoquinoline, imidazole, benzimidazole, azabenzimidazole, benzotriazole, furan, benzofuran, thiazole, benzothiazole, oxazole, benzoxazole, pyrrole, indole, indoline, indazole, pyrrolidine, pyrrolidone, pyrroline, piperidine, piperazine, tetrahydroquinoline, tetrahydroisoquinoline, pyrazole, thiophene, isoxazole, isothiazole, triazole, tetrazole, oxadiazole, thiadiazole, morpholine, thiamorpholine, pyrazolidine, imidazolidine, imidazoline, tetrahydropyran, dihydropyran, benzopyran, dioxane, dithiane, tetrahydrofuran, tetrahydrothiophene, dihydrofuran, dihydrothiophene, etc. Oxides of the nitrogen and sulfur containing heterocycles are also included in the present invention.

The optional substituents on $Ar^2$ include alkyl (1–6C), alkenyl (1–6C), alkynyl (1–6C), halo, nitro, cyano, carboxylic acid, carboxylic ester formed from an alcohol with 1–6C or amide formed from an amine of 0–12C, a sulfonic or sulfinic acid or ester or amide, OR, SR, $NR_2$, OCR, OOCR, NRCOR, all wherein R is hydrogen or straight or branched chain alkyl (1–6C), an optionally substituted aromatic or heterocyclic group, $CF_3$, and the like.

Preferred substituents include alkyl, OR, $NR_2$, and halo. Preferred embodiments of $Ar^2$ include phenyl, pyridinyl, pyrimidinyl and imidazolyl.

In Formula 1, $Ar^1$ is a 5–6 membered aromatic system which is bivalent benzene, pyridine, thiophene, pyrimidine, and the like. $Ar^1$ may optionally be substituted by alkyl, alkenyl, halo, nitro, cyano, $CF_3$, COOR, $CONR_2$, OCR, OOCR, NRCOR, OR, $NR_2$, SR, (where R is H or alkyl 1–6C) sulfonic or sulfinic acids, esters or amides and the like. Preferred embodiments of $Ar^1$ are phenylene, especially 1,3 and 1,4 phenylene and pyridinylene, preferably 2,6 pyridinylene, and 3,5 pyridinylene. Preferable substituents are alkyl, OR, $NR_2$ and halo.

Further, in the compounds of Formula 1, it is preferred that each R group be hydrogen or alkyl of 1–2C, preferably hydrogen. In another preferred embodiment, the R group coupled to a nitrogen is hydrogen or alkyl 1–6C, preferably straight chain alkyl 1–3C, more preferably H or methyl. In other preferred embodiments, 1, 2, 3, 4, or 5 of the R groups are methyl or ethyl and the remaining R groups are hydrogen.

Thus, in one preferred embodiment, the compound of Formula 1 is of the formula V—$CH_2$—$Ar^1$—$CH_2$NR—$CH_2$—$Ar^2$ wherein V is (a) substituted with halo or =O or (b) contains O or S or (c) both (a) and (b), and wherein $Ar^1$ is unsubstituted 1,3 or 1,4-phenylene, R is H, methyl or ethyl and $Ar^2$ is unsubstituted phenyl or pyridinyl.

Preferred embodiments of x are 0–2 and 1–2.

In the treatment or prevention of conditions which require chemokine receptor modulation an appropriate dosage level will generally be about 0.01 to 500 mg per kg body weight per day which can be administered in singe or multiple doses.

Preferably, the dosage level will be about 0.1 to about 250 mg/kg per day. It will be understood that the specific dose level and frequency of dosage for any particular subject may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

Thus, the active compounds may be administered in the form of a pharmaceutical composition formulated according to well known principles and incorporating the compound, preferably in unit dose form, in combination with a pharmaceutically acceptable diluent, carrier or excipient. Such compositions may be in the form of solutions or suspensions for injection, or irrigation or be in capsule, tablet, dragee, or other solid composition or as a solution or suspension for oral administration or formulated into pessaries or suppositories or sustained release forms of any of the above for implantation. Suitable diluents, carriers, excipients and other components are well known. It may be desirable also to formulate a composition for topical administration such as an ointment or cream.

The pharmaceutical compositions according to the invention may be formulated in unit dosages determined in accordance with conventional pharmacological methods, suitably to provide active compounds in the dosage range in humans or animals of from 0.01 to 100 mg/kg body weight per day, in a single dose or in a number of smaller doses. Preferred dosage ranges are 0.01 to 30 mg/kg body weight per day intravenous (iv) or intraperitoneal (ip). Other active compounds may be used in the compositions or such active compounds or supplemental therapy may be included in a course of treatment. The pharmaceutical compositions are useful for treatment of a patient comprising an effective therapeutic amount of the novel compound, where said compound effectively binds to a chemokine receptor.

The present invention further contemplates the use of these compositions in the manufacture of a medicament for the treatment of HIV- or FIV-infected patients and/or the treatment of a disease by the regulation of endothelial cell function and/or the treatment of a disease relating to vascularization of the gastrointestinal tract; haematopoiesis; or cerebellar development.

In a method for treating a patient infected with HIV or FIV, the pharmaceutical composition is administered to said patient as a therapeutically effective amount of a pharmaceutical composition in a pharmaceutically acceptable carrier. In a method of treating a patient with a disease related to the regulation of endothelial cell function, the pharmaceutical composition is administered to said patient as a therapeutically effective amount of a pharmaceutical composition in a pharmaceutically acceptable carrier. The present invention further contemplates methods of treating a patient with a disease relating to vascularization of the gastrointestinal tract; haematopoiesis; or cerebellar development, by administering to said patient a therapeutically effective amount of a pharmaceutical composition in a pharmaceutically acceptable carrier.

The present invention further contemplates a method of treating a patient with a disease relating to basal leukocyte trafficking or the extravasation and tissue infiltration of leukocytes in response to inciting antigens, by administering to said patient a therapeutically effective amount of a pharmaceutical composition in a pharmaceutically acceptable carrier. The present method also contemplates treating a patient, by administering to said patient a therapeutically effective amount of a pharmaceutical composition in a pharmaceutically acceptable carrier, wherein said compound effectively binds to a chemokine receptor.

The present invention further contemplates pharmaceutical compositions and methods of use for the treatment of humans or animals for: renal allograft rejection; inflammatory disease; cancer; central nervous system developmental disease; HIV; vasculature development disease; haematopoiesis and other chemokine mediated diseases or disorders. The invention further provides for the treatment of diseases, which include, but are not limited to: arthritis; asthma; multiple sclerosis; dementia from HIV or FIV infection, Parkinson's disease, Alzheimer's disease and inflammatory diseases. The pharmaceutical compositions and methods of use of the present invention further provide for the treatment of cancers, that include, but are not limited to those associated with: solid tumors; lymphoma; metastatic tumors; glioblastoma tumors; leukemia; and other carcinomas tumors. The pharmaceutical compositions of the present invention are useful for the treatment of cancers that include, but are not limited to: non-small cell lung cancer; lung cancer; breast cancer; prostate cancer; and cancer of other organs.

Other diseases or disorders that are contemplated to be treated with the pharmaceutical compositions of the present invention, include, but are not limited to: disorders treated by inhibiting or promoting angiogenesis or by inducing stasis of angiogenesis; developmental disorders mediated by chemokines.

The present invention further provides methods for the prevention of a disease or disorder in a patient by administering a therapeutically effective dosage of the pharmaceutical compositions of the present invention to a patient over a period of time sufficient to effectively prevent the disease or disorder.

The following examples are intended to illustrate but not to limit the invention.

EXAMPLE 1

Preparation of N-[4-(11-Fluoro-1,4,7-triazacyclotetradecanyl)-1,4-phenylenebis(methylene)]-2-(aminomethyl)pyridine. (AMD8897, FIG. 1)

Acetic acid, 7-acetoxy-4-hydroxy-heptyl ester

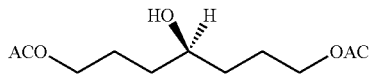

To a solution of heptane-1,4,7-triol (162 mg, 1.09 mmol) in pyridine (4 ml) was added acetic anhydrous (216 mg, 2.28 mmol) at 0° C. The resulting mixture was allowed to stir for 4 hours at 0° C. and then diluted with ethyl acetate (100 ml). The organic solution was washed with sat. NaHCO₃, brine and dried over Na₂SO₄. Evaporation of the solvent and purification of the residue by column chromatography on silica gel, using 30% ethyl acetate in hexanes, gave the title compound (120 mg, 50%) as a colorless oil. $^{1}$H NMR (CDCl₃) δ 1.41–1.86 (m, 8H), 2.05 (s, 6H), 3.62–3.70 (m, 1H), 4.11 (t, 4H, J=6.6 Hz); $^{13}$C NMR (CDCl₃) δ 21.01, 24.92, 33.82, 64.41, 71.06, 171.20.

Acetic acid, 7-acetoxy-4-fluoro-heptyl ester

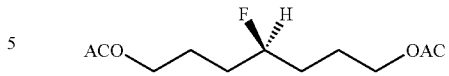

To a solution of (diethylamino)-sulfur trifluoride (571 mg, 3.54 mmol) in CH₂Cl₂ was added the solution of acetic acid, 7-acetoxy-4-hydroxy-heptyl ester (403 mg, 1.74 mmol) in CH₂Cl₂ (10 ml) at –78° C. The resulting mixture was allowed to stir for 15 minutes at –78° C., 30 minutes at room temperature and then diluted with ethyl acetate (300 ml). The organic solution was washed with sat. NaHCO₃, brine and dried over Na₂SO₄. Evaporation of the solvent and purification of the residue by column chromatography on silica gel, using 15% ethyl acetate in hexanes, gave the title compound (386 mg, 94%) as a colorless oil. $^{1}$H NMR (CDCl₃) δ 1.55–1.83 (m, 8H), 2.05 (s, 6H), 4.05–4.15 (m, 4H), 4.39–4.63 (m, 1H); $^{13}$C NMR (CDCl₃) δ 20.97, 24.42, 24.48, 31.51, 31.79, 64.03, 92.22, 94.45, 171.12; $^{19}$F NMR (CDCl₃) δ –106.44–105.27(m); ES-MS m/z 257.3 (M+Na).

4-Fluoro-heptane-1,7-diol

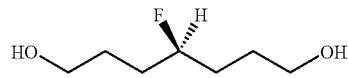

Methanol (15 ml) saturated with anhydrous NH₃ gas was added to acetic acid, 7-acetoxy-4-fluoro-heptyl ester (500 mg, 2.13 mg) contained in round-bottomed flask closed by glass stopper. The mixture was allowed to stir for over 28 hours at room temperature and then concentrated. Purification of the residue by column chromatography on silica gel, using 5% methanol in CH₂Cl₂, gave the title compound (320 mg, 100%) as pure colorless oil. $^{1}$H NMR (CDCl₃) δ 1.59–1.83 (m, 8H), 3.67 (t, 4H, J=5.7 Hz), 4.47–4.67 (m, 1H); $^{13}$C NMR (CDCl₃) δ 28.73, 28.75, 31.78, 32.06, 62.88, 93.56, 95.98; ES-MS m/z 173.2 (M+Na).

1,7-Bis(toluene-4-sulfonic acid)-4-fluoro-heptyl-ester

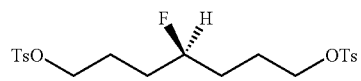

To a pre-cooled (ice bath) solution of 4-fluoro-heptane-1,7-diol (320 mg, 2.13 mmol) and triethylamine (1.0 ml, 6.90 mmol) in CH₂Cl₂ (10 ml) was added a solution of p-toluensulfonyl chloride (812 mg, 4.27 mmol) in CH₂Cl₂ (2 ml). The resulting mixture was stirred for 18 hours at room temperature and then diluted with ethyl acetate (200 ml). The organic solution was washed with sat. NaHCO₃, brine and dried over Na₂SO₄. Evaporation of the solvent and purification of the residue by column chromatography on silica gel, using 20% ethyl acetate in hexanes, gave the title compound (627 mg, 100%) as a colorless oil. $^{1}$H NMR (CDCl₃) δ 1.52–1.86 (m, 8H), 2.45 (s, 6H), 4.00–4.08 (m, 4H), 4.28–4.44 (m, 1H), 7.37 (d, 4H, J=8.4 Hz), 7.77 (d, 4H, J=8.4 Hz); $^{13}$C NMR (CDCl₃) δ 22.06, 25.09, 25.15, 31.32, 31.60, 70.34, 91.97, 94.21, 128.29, 130.30, 133.36, 145.28; $^{19}$F NMR (CDCl₃) δ –107.54–107.02 (m); ES-MS m/z 481.3 (M+Na).

[11-Fluoro-1,7-bis(2-nitro-benzenesulfonyl)-1,4,7-triaza-cyclotetradec-4-yl]-phosphonic acid diethyl ester

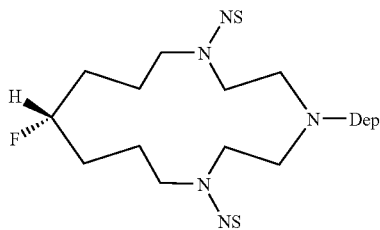

To a stirred solution of bis-[2-(2-nitro-benzenesulfonylamino)-ethyl]-phosphoramidic acid diethyl ester (1.07 g, 1.75 mmol) and anhydrous $Cs_2CO_3$ (1.5 g, 4.60 mmol) in anhydrous DMF (100 ml) at 80° C. under $N_2$ was added a solution of 1,7-bis(toluene-4-sulfonic acid)-4-fluoro-heptyl-ester (687 mg, 1.49 mmol) in DMF (10 ml) over 10 hours. The reaction mixture was allowed to stir at 85° C. for further 30 hours, cooled to room temperature and then concentrated. The residue was diluted with 200-ml ethyl acetate and washed with a sat. $NaHCO_3$ brines and dried over $Na_2SO_4$. Evaporation of the solvent and purification of the residue by column chromatography on silica gel using 50% ethyl acetate in $CH_2Cl_2$ gave the title compound (560 mg, 55%) as a light yellow solid. $^1H$ NMR ($CDCl_3$) δ 1.31 (ddd, 6H, J=0.6, 7.2, 7.2 Hz), 1.65–1.89 (m, 8H), 3.22–3.46 (m, 12H), 3.93–4.14 (m, 4H), 4.67–4.83 (m, 1H), 7.60–7.65 (m, 2H), 7.68–7.75 (m, 4H), 7.99–8.05 (m, 2H); $^{13}C$ NMR ($CDCl_3$) δ 16.54, 16.64, 22.65, 22.74, 29.66, 29.95, 47.04, 47.37, 47.43, 50.22, 63.17, 63.25, 91.38, 93.62, 124.59, 131.67, 131.96, 132.06, 134.22, 148.69; $^{19}F$ NMR ($CDCl_3$) δ −99.84–99.41 (m); ES-MS m/z 724.6 (M+H).

11-Fluoro-1,7-bis-(2-nitro-benzenesulfonyl)-1,4,7-triazacyclotetradecane

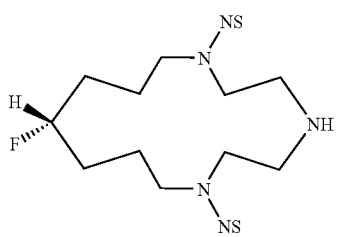

Acetic acid (15 ml), saturated with anhydrous hydrogen bromide (gas) was added to [11-fluoro-1,7-bis(2-nitro-benzenesulfonyl)-1,4,7-triaza-cyclotetradec-4-yl]-phosphonic acid diethyl ester (560 mg, 0.77 mmol) contained in round-bottomed flask closed by glass stopper. The resulting mixture was allowed to stir for 18 hours at room temperature and then diethyl ether (50 ml) was added. The white precipitate which formed was allowed to settle to the bottom of the flask and the diethyl ether solution was decanted off. This white solid was re-dissolved in methanol, stirred with $K_2CO_3$ (solid) for 30 mins then diluted with 100-ml ethyl acetate, and the solids were removed by filtration. Evaporation of the filtrates gave the title compound (454 mg, 100%) as white foam. $^1H$ NMR ($CDCl_3$) δ 1.75–1.99 (m, 8H), 2.90 (t, 4H, J=5.0 Hz), 3.26–3.39 (m, 8H), 4.61–4.77 (m, 1H), 7.60–7.65 (m, 2H), 7.68–7.72 (m, 4H), 7.94–7.97 (m, 2H); ES-MS m/z 588.3 (M+H).

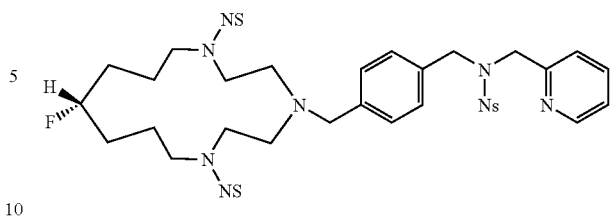

To a stirred solution of 11-fluoro-1,7-bis-(2-nitrobenzenesulfonyl)-1,4,7-triaza-cyclotetradecane (454 mg, 0.77 mmol) and anhydrous $K_2CO_3$ (400 mg, 2.89 mmol) in anhydrous $CH_3CN$ (7 ml) under $N_2$ was added N-[1-methylene-4-(chloromethylene)phenylene]-N-(2-nitrobenzenesulfonyl)-2-(aminomethyl)pyridine (Bridger, et al., U.S. Ser. No. 09/111,895) (743 mg, 1.72 mmol). The reaction mixture was allowed to stir at 85° C. for further 18 hours and then concentrated. The residue was diluted with 100-ml ethyl acetate and washed with a sat. $NaHCO_3$, then brines and dried over $Na_2SO_4$. Evaporation of the solvent and purification of the residue by column chromatography on silica gel using 50% ethyl acetate in $CH_2Cl_2$ gave the title compound (445 mg, 59%) as white form. $^1H$ NMR ($CDCl_3$) δ 1.67–1.83 (m, 8H), 2.69–2.76(m, 4H), 3.19 (td, 4H, J=8.1, 8.1 Hz), 3.34 (t, 4H, J=6.2 Hz), 3.75 (s, 2H), 4.50 (s, 2H), 4.60 (s, 2H), 4.59–4.80 (m, 1H), 7.08–7.20 (m, 7H), 7.51–7.73 (m, 9H), 7.81 (dd, 2H, J=1.8, 7.5 Hz), 8.01 (d, 1H, J=7.8 Hz), 8.38 (d, 1H); $^{19}F$ NMR ($CDCl_3$) δ −99.61–98.50 (m); ES-MS m/z 983.3 (M+H).

N-[4-(11-Fluoro-1,4,7-triazacyclotetradecanyl)-1,4-phenylenebis(methylene)]-2-(aminomethyl)pyridine (AMD8897)

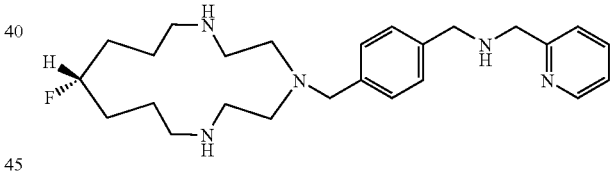

To a stirred solution of the intermediate from above (445 mg, 0.45 mmol) and anhydrous $K_2CO_3$ (750 mg, 5.43 mmol) in anhydrous DMF (6 ml) under $N_2$ was added dropwise, thiophenol (348 mg, 3.17 mmol). The reaction mixture was allowed to stir at room temperature for further 4 hours and then concentrated. The residue was diluted with 100-ml ethyl acetate and solids were removed by filtration through a short column of celite. Evaporation of the solvent and purification of the residue on a chromatron using silica gel (1 mm plate) and an eluent of 1:1:98 Methanol/$NH_4OH$/$CH_2Cl_2$ gave AMD8897 (80 mg, 62%). $^1H$ NMR ($CDCl_3$) δ 1.52–1.85 (m, 8H), 2.53–2.63 (m, 12H), 3.57 (s, 2H), 3.83 (s, 2H), 3.93 (s, 2H), 5.07–5.30 (m, 1H), 7.14–7.33 (m, 6H), 7.64 (ddd, 1H, J=1.8, 7.8, 7.8 Hz), 8.55–8.57 (m, 1H); $^{13}C$ NMR ($CDCl_3$) δ 24.43, 32.13, 32.41, 47.32, 48.47, 52.44, 53.21, 54.52, 58.92, 121.94, 122.32, 128.26, 128.87, 136.42, 137.80, 139.04, 149.33, 159.75; $^{19}F$ NMR ($CDCl_3$) δ −102.30–103.00 (m); ES-MS m/z 428.3 (M+H); Anal. Calcd. for ($C_{25}H_{38}FN_5$): C, 70.22; H, 8.96; N, 16.38. Found: C, 69.99; H, 8.96; N, 16.42.

EXAMPLE 2

Preparation of N-[4-(11,11-difluoro-1,4,7-triazacyclotetradecanyl)-1,4-phenylenebis(methylene)]-2-(aminomethyl)pyridine. (AMD8880, FIG. 2)

4,4-Difluoro-heptanedioic acid diethyl ester

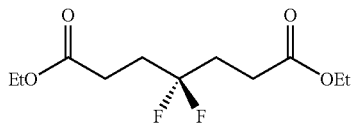

To a neat solution of (diethylamino)-sulfur trifluoride (2.02 g, 12.55 mmol) in a plastic bottle was added 4-oxo-heptanedioic acid diethyl ester (2.56 g, 11.13 mmol) at room temperature. The resulting mixture was allowed to stir for 12 days and then diluted with ethyl acetate (500 ml). The organic solution was washed with sat. NaHCO$_3$, brine and dried over Na$_2$SO$_4$. Evaporation of the solvent and purification of the residue by column chromatography on silica gel, using 20% ethyl acetate in hexanes, gave the title compound (1.2 g, 43%) as pure colorless oil. $^1$H NMR (CDCl$_3$) δ 1.26 (t, 6H, J=8.0 Hz), 2.11–2.28 (m, 4H), 2.52 (t, 4H, J=7.8 Hz), 4.16 (q, 4H, J=4H); $^{19}$F NMR (CDCl$_3$) δ −25.78–25.42(m); $^{13}$C NMR (CDCl$_3$) δ 14.16, 27.09, 27.16, 27.22, 31.52, 31.85, 32.19, 60.80, 120.18, 123.38, 126.58, 172.26; ES-MS m/z 275.1 (M+Na).

4,4-Difluoro-heptane-1,7-diol

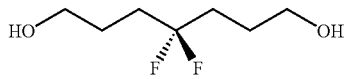

To a solution of 4,4-difluoro-heptanedioic acid diethyl ester (1.3 g, 5.65 mmol) in diethyl ether (35 ml) at 0° C. under N$_2$ was slowly added solid LAH (638 mg, 11.80 mmol). The resulting mixture was allowed to stir for 30 mins at room temperature and then heated to reflux for two hours. Upon cooling, water (0.5 ml) was added, followed by 15% NaOH (0.5 ml) and water (1.5 ml). The resulting mixture was stirred for another two hours at room temperature and then diluted with ethyl acetate (500 ml). The organic solution was dried over Na$_2$SO$_4$ without aqueous work-up. Evaporation of the solvent gave the title compound (646 g, 68%) as pure colorless oil. $^1$H NMR (CDCl$_3$) δ 1.71–1.80 (m, 4H), 1.87–2.03 (m, 4H), 3.69 (t, 4H, J=60 Hz); $^{19}$F NMR (CDCl$_3$) δ −22.64–22.28(m); $^{13}$C NMR (CDCl$_3$) δ 25.81, 25.87, 25.92, 32.99, 33.33, 33.67, 122.38, 125.56, 128.74.

1,7-bis(Toluene-4-sulfonic acid)-4,4-difluoro-heptyl-ester

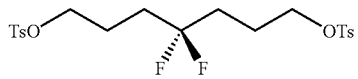

To a pre-cooled (ice bath) solution of 4,4-difluoro-heptane-1,7-diol (450 mg, 2.67 mmol) and triethylamine (1.2 ml, 8.31 mmol) in CH$_2$Cl$_2$ (5 ml) was added a solution of p-toluensulfonyl chloride (1.13 g, 5.94 mmol) in CH$_2$Cl$_2$ (2 ml). The resulting mixture was allowed to stir for 18 hours at room temperature and then diluted with ethyl acetate (200 ml). The organic solution was washed with sat. NaHCO$_3$, then brine and dried over Na$_2$SO$_4$. Evaporation of the solvent and purification of the residue by column chromatography on silica gel, using 20% ethyl acetate in hexanes, gave the title compound (1.1 g, 83%) as a colorless oil. 1H NMR (CDCl$_3$) δ 1.75–1.90 (m, 8H), 2.44 (s, 6H), 4.01–4.05 (m, 4H), 7.33 (d, 4H, J=8.1 Hz), 7.75 (d, 4H, J=8.1 Hz); $^{19}$F NMR (CDCl$_3$) δ −24.27 (t); $^{13}$C NMR (CDCl$_3$) δ 22.06, 22.22, 22.28, 22.34, 32.80, 33.14, 33.48, 33.71, 69.96, 70.07, 121.06, 124.26, 127.46, 128.27, 130.36,133.18, 145.42. ES-MS m/z 477.1 (M+H).

[11,11-Difluoro-1,7-bis(2-nitro-benzenesulfonyl)-1,4,7-triazacyclotetradec-4-yl]-phosphonic acid diethyl ester

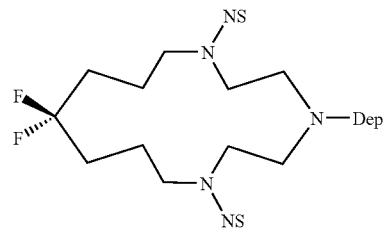

To a stirred solution of bis-[2-(2-nitrobenzenesulfonylamino)-ethyl]-phosphoramidic acid diethyl ester (1.5 g, 2.46 mmol) and anhydrous Cs$_2$CO$_3$ (2.2 g, 6.74 mmol) in anhydrous DMF (150 ml) at 80° C. under N$_2$ was added a solution of 1,7-bis(toluene-4-sulfonic acid)-4,4-difluoro-heptyl-ester (1.07 mg, 2.25 mmol) in DMF (10 ml) over 10 hours. The reaction mixture was allowed to stir at 85° C. for a further 30 hours, cooled to room temperature and then concentrated. The residue was diluted with 200-ml ethyl acetate and washed with a sat. NaHCO$_3$, then brines and dried over Na$_2$SO$_4$. Evaporation of the solvent and purification of the residue by column chromatography on silica gel using 50% ethyl acetate in CH$_2$Cl$_2$ gave the title compound (311 mg, 19%) as a light yellow solid. $^1$H NMR (CDCl$_3$) δ 1.32 (t, 6H, J=7.1 Hz), 1.72–1.79 (m, 4H), 1.95–2.05 (m, 4H), 3.30 (s, 4H), 3.32 (s, 4H), 340 (t, 4H, J=6.15), 3.96–4.08 (m, 4H), 7.60–7.66 (m, 2H), 7.69–7.76 (m, 4H), 799–805 (m, 2H); $^{19}$F NMR (CDCl$_3$) δ −14.87–14.61 (m); $^{13}$C NMR (CDCl$_3$) δ 16.54, 16.63, 22.52, 32.07, 32.42, 32.77, 47.16, 47.89, 47.95, 50.17, 63.19, 63.27, 122.42, 124.65, 124.87, 125.67, 128.87, 131.55, 131.60, 132.16, 134.44, 148.72; ES-MS m/z 742.2 (M+H).

11,11-Difluoro-1,7-bis-(2-nitrobenzenesulfonyl)-1,4,7-triazacyclotetradecane

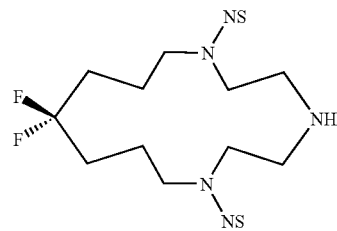

Acetic acid (10 ml), saturated with anhydrous hydrogen bromide (gas) was added to [11,11-difluoro-1,7-bis(2-nitrobenzenesulfonyl)-1,4,7-triaza-cyclotetradec-4-yl]-phosphonic acid diethyl ester (311 mg, 0.41 mmol) contained in round-bottomed flask closed by glass stopper. The resulting mixture was allowed to stir for 18 hours at room temperature and then diethyl ether (50 ml) was added. The white precipitate which formed was allowed to settle to the bottom of the flask and the diethyl ether solution was decanted off. This white solid was re-dissolved in methanol, stirred with $K_2CO_3$ (solid) for 30 mins and the mixture was diluted with 100-ml ethyl acetate. The solids were removed by filtration and the filtrates were evaporated to give the title compound (239 mg, 94%) as white form. 1H NMR (CDCl$_3$) δ 1.82–1.91 (m, 4H), 1.99–2.15 (m, 4H), 2.91 (t, 4H, J=5.1 Hz), 3.30–3.38 (m, 8H), 7.60–7.63 (m, 2H), 7.69–7.75 (m, 4H), 7.90–7.94 (m, 2H); $^{13}$C NMR (CDCl$_3$) δ 23.25, 32.22, 32.57, 32.90, 50.22, 50.86, 50.96, 123.50, 124.60, 126.71, 129.89, 130.73, 132.02, 132.22, 134.27, 148.94; $^{19}$F NMR (CDCl$_3$) δ −14.12 (t); ES-MS m/z 606.3 (M+H).

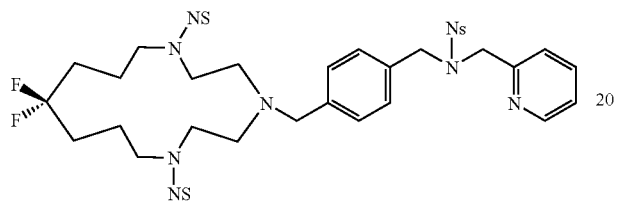

To a stirred solution of 11,11-difluoro-1,7-bis-(2-nitrobenzenesulfonyl)-1,4,7-traiazacyclotetradecane (239 mg, 0.39 mmol) and anhydrous $K_2CO_3$ (320 mg, 2.30 mmol) in anhydrous $CH_3CN$ (4 ml) under $N_2$ was added N-[1-methylene-4-(chloromethylene)phenylene]-N-(2-nitrobenzenesulfonyl)-2-(aminomethyl)pyridine (Bridger et al. U.S. Ser. No. 09/111,895) (512 mg, 1.18 mmol). The reaction mixture was allowed to stir at 85° C. for further 18 hours and then concentrated. The residue was diluted with 100-ml ethyl acetate and washed with a sat. NaHCO$_3$, then brines and dried over Na$_2$SO$_4$. Evaporation of the solvent and purification of the residue by column chromatography on silica gel using 50% ethyl acetate in CH$_2$Cl$_2$ gave the title compound (289 mg, 73%) as white foam. $^1$H NMR (CDCl$_3$) δ 1.73–1.77 (m, 4H), 1.89–1.99 (m, 4H), 2.75 (t, 4H, J=6.8 Hz), 3.24 (t, 4H, J=7.5 Hz), 3.34 (t, 4H, J=6.3 Hz), 3.58 (s, 2H), 4.56 (s, 2H), 4.59 (s, 2H), 7.08–7.18 (m, 6H), 7.52–7.75 (m, 10H), 7.83 (dd, 2H, J=1.5, 7.8 Hz), 7.99 (d, 1H, J=7.8 Hz), 8.40 (d, 1H); $^{13}$C NMR (CDCl$_3$) δ 22.43, 32.32, 46.84, 48.99, 51.71, 52.36, 54.65, 59.30, 122.90, 122.96, 124.57, 124.61, 128.93, 129.76, 130.35, 131.12, 131.49, 132.12, 132.24, 133.83, 134.14, 134.29, 134.45, 134.84, 137.06, 138.30, 148.33, 148.63, 149.68, 155.96; $^{19}$F NMR (CDCl$_3$) δ −14.52 (t); ES-MS m/z 1001.3 (M+H).

N-[4-(11,11-difluoro-1,4,7-triazacyclotetradecanyl)-1,4-phenylenebis(methylene)]-2-(aminomethyl)pyridine (AMD8880).

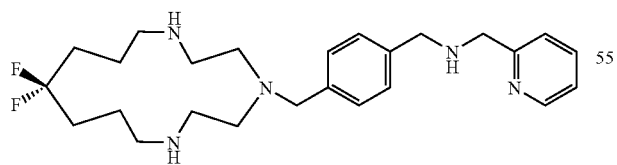

To a stirred solution of the intermediate from above (289 mg, 0.29 mmol) and anhydrous $K_2CO_3$ (478 mg, 3.46 mmol) in anhydrous DMF (4 ml) under $N_2$ was added dropwise, thiophenol (222 mg, 2.02 mmol). The reaction mixture was allowed to stir at room temperature for a further 4 hours and then concentrated. The residue was diluted with 100-ml ethyl acetate and solids were removed by filtration through a short column of celite. Evaporation of the solvent and purification of the residue on a chromatron using silica gel (1 mm plate) eluted with 1:1:98 Methanol/NH$_4$OH/CH$_2$Cl$_2$ gave AMD8880 (80 mg, 62%) as a light yellow oil. $^1$H NMR (CDCl$_3$) δ 1.63–1.72 (m, 4H), 2.00–2.15 (m, 4H), 2.60–2.65 (m, 12H), 3.57 (s, 2H), 3.83 (s, 2H), 3.93 (s, 2H), 7.14–7.18 (m, 1H), 7.20–7.34 (m, 5H), 7.60–7.67 (m, 1H), 8.55 (d, 1H, J=4.8 Hz); $^{13}$C NMR (CDCl$_3$) δ 23.47, 32.64, 32.98, 33.32, 47.69, 48.66, 53.61, 54.21, 54.94, 59.67, 122.32, 122.71, 127.03, 128.59 129.28, 136.81, 138.49, 139.36, 149.71, 160.16; $^{19}$F NMR (CDCl$_3$) δ −15.50 (q, J=12.65 Hz); ES-MS m/z 446.4 (M+H); Anal. Calcd. for (C$_{25}$H$_{37}$F$_2$N$_5$): C, 67.39; H, 8.37; N, 15.72. Found: C, 67.52; H, 8.49; N, 15.43.

EXAMPLE 3

Preparation of N-[4-(1,4,7-triazacyclotetradecan-2-one)-yl))-1,4-phenylenebis(methylene)]-2-(aminomethyl)pyridine (hydrobromide salt).
(AMD8748, FIG. 3)

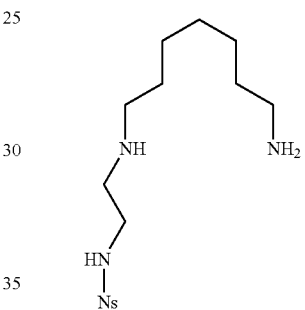

Nosylaziridine 11.7 g (51.3 mmol) in anhydrous THF (80 ml) was added dropwise to a stirred solution of 1,7-diaminoheptane 33.4 g (256.3 mmol) in anhydrous THF (220 ml). After completion of addition, the mixture was stirred for 20 min at room temperature under nitrogen atmosphere. The solution was concentrated in vacuo to afford crude product as a yellow oil. The oil was purified by flash chromatography on silica gel eluting with 5% MeOH, 5% NH$_4$OH, 90% CH$_2$Cl$_2$ to give the desired amine as a yellow oil (10.9 g, 59%). $^1$H NMR (CDCl$_3$, 300 MHz) δ 1.27–1.50 (m, 10 H), 2.09 (s, 4H), 2.47 (t, J=6.0 Hz, 2H), 2.68 (t, J=7.5 Hz, 2H), 2.75 (t, J=6.0 Hz, 2H), 3.13 (t, J=6.0 Hz, 2H), 7.72–7.75 (m, 2H), 7.75–7.87 (m, 1H), 8.13–8.16 (m, 1H); exact mass calculated for C$_{15}$H$_{26}$N$_4$O$_4$S: 358. found: m/z 359 [M+H]$^+$.

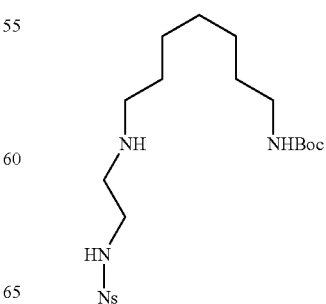

To a stirred solution of the amine from above (7.0 g, 19.5 mmol) and 4.3 ml (29.3 mmol) of Et₃N in THF (300 ml) at −78° C. was added dropwise 4.3 g (19.5 mmol) of Boc₂O in THF (100 ml). After 1 h the reaction mixture was diluted with EtOAc, and washed with aqueous NaHCO₃, dried (MgSO₄), and concentrated in vacuo. Purification by flash chromatography on silica gel eluting with 5% MeOH, 95% CH₂Cl₂ gave 5.6 g (63%) of the desired BOC intermediate as a pale yellow oil. ¹H NMR (CDCl₃, 300 MHz) δ 1.26–1.27 (m, 10 H), 1.36–1.44 (m, 9H), 2.47 (t, J=7.5 Hz, 2H), 2.75 (t, J=6.0 Hz, 2H), 3.00 (br s, 2H), 3.06–3.16 (m, 4H), 4.50 (br s, 1H), 7.72–7.76 (m, 2H), 7.86–7.89 (m, 1H), 8.13–8.16 (m, 1H); exact mass calculated for $C_{20}H_{34}N_4O_6S$: 458. found: m/z 459 [M+H]⁺.

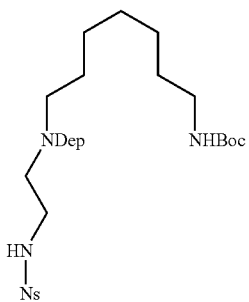

To a stirred solution of the BOC intermediate from above (1.6 g, 3.49 mmol) and 1.5 ml (10.5 mmol) of Et₃N in 100 ml of anhydrous CH₂Cl₂ was added 504 ul (19.5 mmol) of DepCl, and the reaction mixture was stirred under a nitrogen atmosphere for 24 h. The solvent was removed under reduced pressure and the residue was dissolved in EtOAc, washed with aqueous NaHCO₃, dried (Na₂SO₄), and concentrated in vacuo. Purification by flash chromatography on silica gel, eluting with 5% MeOH, 95% CH₂Cl₂ gave 1.4 g (67%) of the Dep intermediate as a pale yellow oil. ¹H NMR (CDCl₃, 300 MHz) δ 1.23–1.34 (m, 16H), 1.44 (s, 9H), 2.88–2.94 (m, 2H), 3.08–3.11 (m, 2H), 3.22 (d, J=6.0 Hz, 4H), 4.00–4.09 (m, 4H), 4.50 (br s, 1H), 6 11 (br s, 1H), 7.72–7.75 (m, 2H), 7.83–7.84 (m, 1H), 8.10–8.13 (m, 1H); exact mass calculated for $C_{24}H_{43}N_4O_9SP$: 594. found: m/z 595 [M+H]⁺.

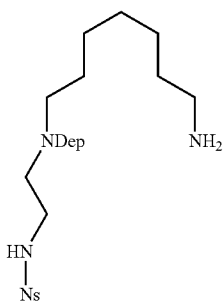

To a stirred solution of the Dep intermediate from above (1.0 g, 1.74 mmol) in 30 ml of anhydrous CH₂Cl₂ was added 10 ml of TFA, and the reaction mixture was stirred under a nitrogen atmosphere for 40 min at room temperature. TFA and the solvent were removed under reduced pressure. The residue was dissolved with MeOH. K₂CO₃ was added to the solution, and the mixture was stirred for 10 min at room temperature. The mixture was diluted with 50 ml of CH₂Cl₂, filtered through celite, and concentrated in vacuo. Purification by flash chromatography on silica gel eluting with 5% MeOH, 5% NH₄OH, 90% CH₂Cl₂ gave 731 mg (85%) of the desired amine as a yellow oil. ¹H NMR (CDCl₃, 300 MHz) δ 1.28–1.33 (m, 12H), 1.42–1.46 (m, 4H), 2.60–2.67 (m, 5H), 2.91 (q, J=8.7 Hz, 2H), 3.20–3.22 (m, 4H), 4.03 (q, J=7.5 Hz, 4H), 7.70–7.73 (m, 2H), 7.81–7.82 (m, 1H), 8.09–8.12 (m, 1H); exact mass calculated for $C_{19}H_{35}N_4O_7SP$: 494. found: m/z 495 [M+H]⁺.

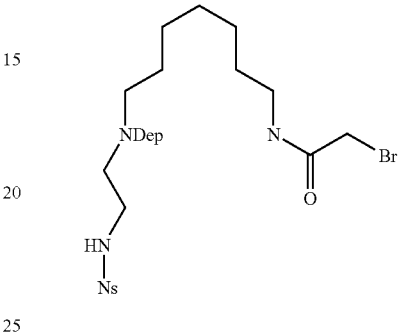

To a stirred solution of the amine from above (731 mg, 1.48 mmol) in 31 ml of anhydrous THF was added 1.6 g (14.7mmol) of Na₂CO₃, and the mixture was cooled to −15° C. Bromoacetyl bromide 155 ul (1.78 mmol) in 1.6 ml of THF was added to the mixture dropwise. After 1 h, a second portion 51 ul (0.59 mmol) of bromoacetyl bromide was added to the solution. The mixture was stirred at −15° C. under a nitrogen atmosphere for a further 30 min. The reaction mixture was diluted with 50 ml of CH₂Cl₂, filtered through celite, and concentrated in vacuo. Purification of the residue by flash chromatography on silica gel eluting with 5% MeOH, 95% CH₂Cl₂ gave 807 mg (89%) of the desired amide as a yellow oil. 1H NMR (CDCl₃, 300 MHz) δ 1.25–1.34 (m, 14H), 1.48–1.53 (m, 2H), 2.94 (q, J=3 Hz, 2H), 3.21–3.31 (m, 6H), 3.88 (s, 2H), 4.01–4.09 (m, 4H), 6.14 (br s, 1H), 6.58 (br s, 1H), 7.72–7.75 (m, 2H), 7.83–7.84 (m, 1H), 8.10–8.13 (m, 1H); exact mass calculated for $C_{21}H_{36}N_4O_8SPBr$: 616. found: m/z 617 [M+H]⁺.

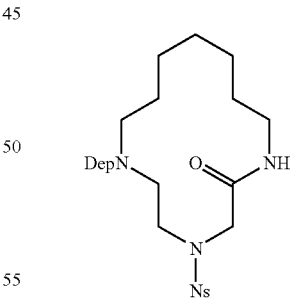

To a stirred solution of the amide from above (369 mg, 0.60 mmol) in 1000 ml of anhydrous acetonitrile was added 417 mg (3.1 mmol) of K₂CO₃, and the mixture was stirred at 60° C. under a nitrogen atmosphere for 24 h. The solution was concentrated under reduced pressure. Purification by flash chromatography on silica gel eluting with 5% MeOH, 5% NH₄OH, 90% CH₂Cl₂ gave 290 mg (90%) of the desired macrocycle as a yellow oil. ¹H NMR (CDCl₃, 300 MHz) δ 1.28 (t, J=7.5 Hz, 6H), 1.30–1.37 (m, 10H), 2.94–2.95 (m, 2H), 3.27–3.45 (m, 6H), 3.96–4.04 (m, 4H), 4.05 (s, 2H), 6.58 (t, J=6.0 Hz, 1H), 7.66–7.68 (m, 1H), 7.73–7.76 (m, 2H), 8.16–8.19 (m, 1H); exact mass calculated for $C_{21}H_{35}N_4O_8SP$: 534. found: m/z 535 [M+H]$^+$.

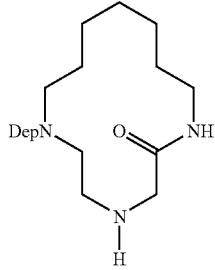

To a stirred solution of the macrocycle from above (290 mg, 0.54 mmol) in 5 ml of anhydrous DMF was added 374 mg (2.71 mmol) of $K_2CO_3$, and 167 µl (1.63 mmol) of thiophenol. The mixture was stirred at room temperature under a nitrogen atmosphere for 4 h. The solution was concentrated under reduced pressure. The residue was dissolved in $CH_2Cl_2$, filtered through celite, and concentrated in vacuo. Purification by flash chromatography on silica gel eluting with 3% MeOH, 5% $NH_4OH$, 92% $CH_2Cl_2$ gave 145 mg (77%) of the macrocyclic amine as a yellow solid. $^1$H NMR (CDCl$_3$, 300 MHz) δ 1.31 (t, J=7.5 Hz, 6H), 1.33–1.59 (m, 10H), 2.70 (t, J=7.5 Hz, 2H), 2.96–2.99 (m, 2H), 3.20–3.34 (m, 5H), 3.31 (s, 2H), 3.96–405 (m, 4H), 7.40 (br s, 1H), exact mass calculated for $C_{15}H_{32}N_3O_4P$: 349. found: m/z 350 [M+H]$^+$.

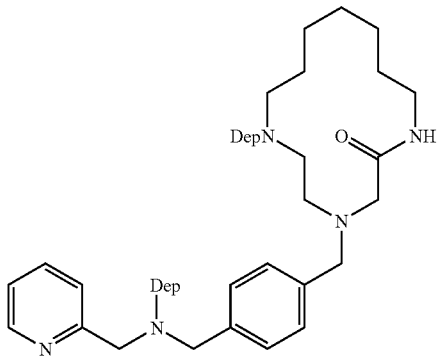

To a stirred solution of the macrocyclic amine from above (152 mg, 0.44 mmol) in 4 ml of anhydrous acetonitrile was added 180 mg (1.31 mmol) of $K_2CO_3$, and 237 mg (0.61 mmol) of N-[1-methylene-4-(chloromethylene)phenylene]-N-(diethoxyphosphoryl)-2-(aminomethyl)pyridine (Bridger et al. U.S. Ser. No. 09/111,895). The mixture was stirred at 83° C. under a nitrogen atmosphere for 18 h. The solution was concentrated under reduced pressure. The residue was dissolved with $CH_2Cl_2$, filtered through celite, and concentrated in vacuo to afford crude product as yellow oil. Purification by flash chromatography on silica gel eluting with 3% MeOH, 97% $CH_2Cl_2$ gave 257 mg (85%) of the desired intermediate as a yellow foam. $^1$H NMR (CDCl$_3$) δ 1.25–1.30 (m, 12H), 1.31–1.61 (m, 10H), 2.50–2.55 (m, 2H), 280–294 (m, 2H), 2.97 (s, 2H), 3.25–3.50 (m, 5H), 3.97 (s, 2H), 4.02–4.12 (m, 8H), 421 (dd, J=16.5 Hz, J=10.5 Hz, 4H), 7.04–7.26 (m, 5H), 7.36 (d, J=6.0 Hz, 1H), 7.62 (t, J=3 Hz, 1H), 8.50 (d, J=3.0 Hz, 1H); exact mass calculated for $C_{33}H_{55}N_5O_7P_2$: 695, found: m/z 696 [M+H]$^+$.

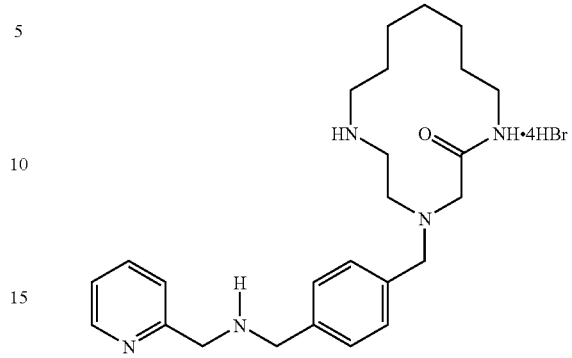

AMD 8748

N-[4-(1,4,7-triazacyclotetradecan-2-one)-yl))-1,4-phenylenebis(methylene)]-2-(aminomethyl)pyridine (AMD8748)

The intermediate from above (257 mg, 0.37 mmol) was dissolved in 3 ml of HBr/AcOH and the solution was stirred at room temperature for 24 h. Diethyl ether was added to the mixture resulting in the formation of a yellow precipitate. The solid was collected by filtration, washed with diethyl ether and dried in vacuo to give AMD8748 as a white powder (182 mg, 60%). $^1$H NMR (D$_2$O, 300 MHz) δ 1.38–1.74 (m, 10H), 3.15 (t, J=7.5 Hz, 2H), 3.26–3.28 (m, 2H), 3.45–3.59 (m, 4H), 3.84 (s, 2H), 4.47 (s, 2H), 4.58 (s, 2H), 7.62–7.76 (m, 5H), 7.79 (d, J=8.7 Hz, 1H), 8.23 (t, J=6.0 Hz, 1H), 8.73 (d, J=5.1 Hz, 1H); $^{13}$C NMR (D$_2$O, 75.5 MHz) δ 167.59, 148.23, 147.32, 142.85, 132.44, 132.21, 131.34, 126.44, 126.39, 59.72, 54.77, 51.20, 50.19, 49.45, 45.49, 40.38, 39.05, 26.89, 24.85, 23.37, 23.16, 21.66; exact mass calculated for $C_{25}H_{37}N_5O$: 423. found: m/z 424 [M+H]$^+$; anal calculated for $(C_{25}H_{37}N_5O)2.5$ (H$_2$O) 3.9 (HBr) 0.4 ($C_4H_{10}O$): C, 39.26; H, 6.18, N, 8.61; Br, 38.29. found: C, 39.15; H, 5.99, N, 8.53; Br, 38.45.

EXAMPLE 4

Preparation of N-[12-(5-oxa-1,9-diazacyclotetradecanyl)-1,4-phenylenebis(methylene)]-2-(aminomethyl)pyridine (hydrobromide salt).
(AMD8922, FIG. 4)

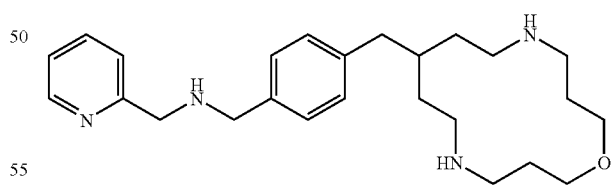

Preparation of 2-(4-cyano-benzyl)-malonic acid dimethyl ester.

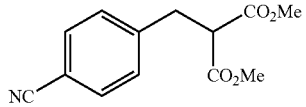

Dimethyl malonate (10.00 g, 75.7 mmol) was added to a suspension of NaH (60% in oil, 3.33 g, 83.3 mmol) in THF (100 mL) over 20 minutes at room temperature. The mixture was heated at 80° C. for 15 minutes, then a solution of α-bromotolunitrile (14.84 g, 75.69 mmol) in THF (100 mL) was added. Heating was continued at 80° C. for 1 hour, then at 50° C. for 64 hours. Water (30 mL) was added, and the aqueous phase was extracted with EtOAc (3×20 mL). The combined organic phases were dried (MgSO$_4$) and concentrated. Purification of the crude material on silica gel (25% EtOAc/hexanes) gave the title compound as colourless crystals (8.49 g, 45%). $^1$H NMR (CDCl$_3$) δ 3.27 (d, 2H, J=9.0 Hz), 3.67 (t, 1H, J=9.0 Hz), 3.70 (s, 6H), 7.32 (d, 2H, J=9.0 Hz), 7.58 (d, 2H, J=9.0 Hz).

N-[4-(3-Hydroxy-2-hydroxymethyl-propyl)-benzyl]-2-nitro-N-pyridin-2-ylmethyl-benzenesulfonamide.

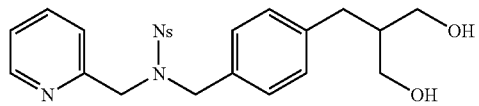

To a solution of 2-(4-cyano-benzyl)-malonic acid dimethyl ester (8.47 g, 34.3 mmol) in THF (30 mL) at 0° C. was added LiAlH$_4$ (1.0 M in THF, 206 mL, 206 mmol), and the mixture was heated at reflux for 19.5 hours. The mixture was cooled to 0° C., and H$_2$O (8 mL) was added dropwise followed by 15% NaOH(aq) (8 mL) and H$_2$O (24 mL). The mixture was stirred at room temperature for 45 minutes, then dried (MgSO$_4$) and filtered. The filtrate was concentrated to give a yellow oil (5.16 g).

A solution of the crude diol (5.13 g) in CH$_2$Cl$_2$ (105 mL) was stirred at 0° C. while Et$_3$N (4.00 mL, 28.7 mmol) was added followed by 2-nitrobenzenesulfonyl chloride (5.90 g, 26.6 mmol). The solution was stirred at room temperature for 17 hours, then washed with brine (70 mL). The aqueous phase was extracted with CH$_2$Cl$_2$ (3×20 mL). The combined organic phases were dried (MgSO$_4$) and concentrated. Purification of the crude material on silica gel (80% THF/hexanes) gave a yellow solid (3.06 g).

The protected diol (2.87 g), 2-picolyl chloride hydrochloride (1.36 g, 8.29 mmol), K$_2$CO$_3$ (3.13 g, 22.6 mmol), and KBr (90 mg, 0.76 mmol) were heated at reflux in acetonitrile (40 mL) for 17.5 hours. Water (30 mL) was added, and the mixture was extracted with EtOAc (100 mL). The organic extract was washed with brine (20 mL), and the combined aqueous phases were extracted with EtOAc (3×20 mL). The combined organic extracts were dried (MgSO$_4$) and concentrated. Purification of the crude material on silica gel (10:10:1 CH$_2$Cl$_2$/EtOAc/MeOH) gave the title compound as a yellow oil (1.83 g, 9% over 3 steps). $^1$H NMR (CDCl$_3$) δ 2.00 (m, 1H), 2.56 (d, 2H, J=7.5 Hz), 3.64 (m, 2H), 3.78 (m, 2H), 4.57 (s, 2H), 4.60 (s, 2H), 7.02–7.14 (m, 5H), 7.23 (d, 1H, J=7.8 Hz), 7.56 (m, 2H), 7.67 (d, 2H, J=3.9 Hz), 7.97 (d, 1H, J=7.8 Hz), 8.41 (d, 1H, J=4.8 Hz).

N-[4-(3-Cyano-2-cyanomethyl-propyl)-benzyl]-2-nitro-N-pyridin-2-ylmethyl-benzenesulfonamide.

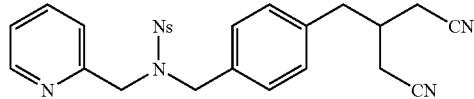

To a solution of N-[4-(3-hydroxy-2-hydroxymethyl-propyl)-benzyl]-2-nitro-N-pyridin-2-ylmethyl-benzenesulfonamide (1.80 g, 3.82 mmol) and Et$_3$N (1.30 mL, 9.33 mmol) in CH$_2$Cl$_2$ (30 mL) at 0° C. was added MsCl (0.65 mL, 8.4 mmol). The solution was stirred at room temperature for 30 minutes, then concentrated. EtOAc (50 mL) was added, and the mixture was washed with H$_2$O (20 mL), saturated NaHCO$_3$(aq) (2×15 mL), and brine (15 mL) then dried (MgSO$_4$) and concentrated to give a yellow oil (2.36 g).

A mixture of the crude mesylate (2.36 g), cetyltrimethylammonium bromide (137 mg, 0.376 mmol), and NaCN (1.3 g, 27 mmol) in 2:1 benzene/H$_2$O (30 mL) was heated at reflux for 18 hours. The mixture was diluted with EtOAc (100 mL) and washed with H$_2$O (20 mL), saturated NaHCO$_3$(aq) (2×20 mL), and brine (10 mL) then dried (MgSO$_4$) and concentrated. Purification of the crude material on silica gel (80% EtOAc/hexanes) gave the title compound as a yellow oil (824 mg, 44% over 2 steps). $^1$H NMR (CDCl$_3$) δ 2.31–2.55 (m, 5H), 2.79 (d, 2H, J=6.0 Hz), 4.59 (s, 2H), 4.60 (s, 2H), 7.04–7.25 (m, 6H), 7.51–7.64 (m, 2H), 7.69 (m, 2H), 8.03 (d, 1H, J=7.8 Hz), 8.41 (d, 1H, J=4.8 Hz).

Methanesulfonic acid 5-methanesulfonyloxy-3-(4-{[(2-nitro-benzenesulfonyl)-pyridin-2-ylmethyl-amino]-methyl}-benzyl)-penyl ester.

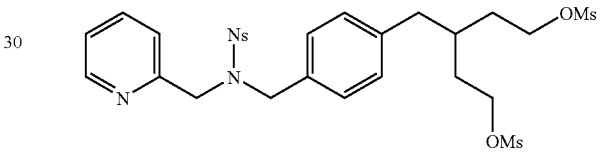

A solution of N-[4-(3-cyano-2-cyanomethyl-propyl)-benzyl]-2-nitro-N-pyridin-2-ylmethyl-benzenesulfonamide (2.36 g, 4.82 mmol) in 4:1 concentrated HCl(aq)/AcOH (25 mL) was heated at reflux for 17 hours. Water (80 mL) was added, and the mixture was extracted with EtOAc (5×25 mL). The organic phase was extracted with saturated NaHCO$_3$(aq) (5×20 mL) and H$_2$O (2×20 mL). The combined aqueous extracts were acidified (pH 1–2) with concentrated HCl(aq) and extracted with EtOAc (5×25 mL). The combined organic extracts were dried (MgSO$_4$) and concentrated to give a brown foam (1.25 g).

To a solution of the crude diacid (1.25 g) in THF (20 mL) was added BH$_3$Me$_2$S (10 M in BH$_3$, 2.9 mL, 29 mmol). The mixture was heated at reflux for 30 minutes. Methanol (30 mL) was added, and the solution was concentrated. The residue was dissolved in MeOH (30 mL) and the solution was concentrated (repeated) to give a yellow foam (1.04 g).

To a solution of the crude diol (1.00 g) and Et$_3$N (1.4 mL, 10 mmol) in CH$_2$Cl$_2$ (20 mL) at 0° C. was added MsCl (0.70 mL, 9.0 mmol). The mixture was stirred at room temperature for 20 minutes, then concentrated. The residue was partitioned between EtOAc (30 mL) and saturated NaHCO$_3$(aq) (15 mL). The organic phase was washed with saturated NaHCO$_3$(aq) (15 mL) and brine (5 mL), then dried (MgSO$_4$) and concentrated. Purification of the crude material on silica gel (10:10:1 CH$_2$Cl$_2$/EtOAc/MeOH) gave the title compound as a yellow oil (450 mg, 15% over 3 steps). $^1$H NMR (CDCl$_3$) δ 1.75 (m, 4H), 2.01 (m, 1H), 2.59 (d, 2H, J=7.2 Hz), 3.00 (s, 6H), 4.23 (m, 4H), 4.58 (s, 2H), 4.59 (s, 2H), 7.02 (d, 2H, J=8.1 Hz), 7.11 (m, 3H), 7.25 (d, 1H, J=8.4 Hz), 7.53–7.61 (m, 2H), 7.69 (m, 2H), 8.00 (m, 1H), 842 (m, 1H).

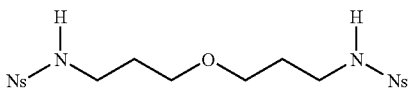

To a solution of bis(3-aminopropyl)ether (1.40 mL, 10 mmol) in dichloromethane (50 mL) was added triethylamine (4.2 mL, 30 mmol) and 2-nitrobenzenesulfonyl chloride (5.42 g, 24 mmol). The resultant solution was stirred at room temperature for four hours. Aqueous ammonium chloride (50 mL) was then added, the organic and aqueous layers were separated and the aqueous layer was extracted twice with dichloromethane. The combined organic layers were then dried and concentrated, and the resultant viscous yellow oil was chromatographed over silica gel using a 5% methanol solution in dichloromethane as an eluant to afford the desired product, bis(3-nitrobenzenesulfonylaminopropyl)ether as a pale yellow oil in a yield of 3.3 g (66%). $^1$H NMR (CDCl$_3$) δ 1.79 (qi, 4H, J=7.1 Hz), 3.16 (t, 4H, J=7.0 Hz), 3.47 (t, 4H, J=7.1 Hz), 5.82 (br s, 2H), 7.71 (m, 8H), 7.83 (d, 2H, J=6.6 Hz), 8.11 (d, 2H, J=6.6 Hz).

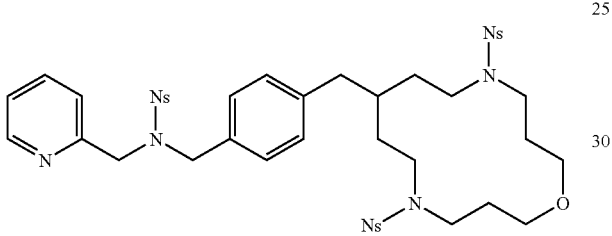

A solution of bis(3-nitrobenzenesulfonylaminopropyl) ether (190 mg, 0.38 mmol) and finely ground, freshly oven-dried cesium carbonate (320 mg, 1.14 mmol) in anhydrous DMF (60 mL) was heated to 80° C. Methanesulfonic acid, 5-methanesulfonyloxy-3-(4-{[(2-nitro-benzenesulfonyl)-pyridin-2-ylmethyl-amino]-methyl}-benzyl)-pentyl ester (250 mg, 0.38 mmol) in DMF (20 mL) was then added to the reaction over a 30 hour period via syringe pump. After complete addition, the reaction was stirred another 30 hours. The mixture was then cooled, diluted with 300 mL ethyl acetate and extracted repeatedly with water. The organic phase was then dried and concentrated, and the residue was purified by column chromatography on silica gel using 25% ethyl acetate in dichloromethane as eluant to afford the desired product (203 mg, 51%). $^1$H NMR (CDCl$_3$) δ 1.47–1.71 (m, 9H), 2.42 (d, 2H, J=6.1 Hz), 3.15–3.32 (m, 12H), 4.53 (s, 2H), 4.55 (s, 2H), 6.94 (d, 2H, J=6.4 Hz), 7.03 (d, 2H, J=6.4 Hz), 7.05 (d, 1H, J=5.8 Hz), 7.52 (m, 4 H), 7.64 (m, 6 H), 7.91 (m, 5H), 8.44 (1H, J=5.4 Hz).

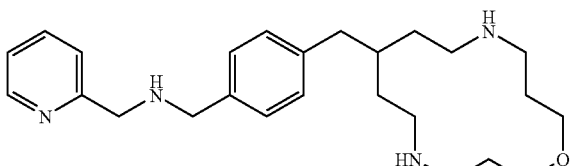

A solution of the intermediate from above (203 mg, 0.203 mmol) in acetonitrile (8 mL) was treated with potassium carbonate (450 mg, 3.05 mmol) and thiophenol (0.25 mL, 2.44 mmol) and the mixture was stirred overnight at room temperature. Following standard work-up, the crude mixture was purified by chromatography on silica gel (85:12:3 dichloromethane:methanol:ammonium hydroxide), the desired product (47 mg, 57%) as a white foam. $^1$H NMR (CDCl$_3$) δ 1.44–1.89 (m, 8H), 1.93 (m, 3H), 2.51 (m, 4H), 2.68 (m, 2H), 2.72 (m, 2H), 3.10 (br s, 2H (NH)), 3.54 (m, 4H), 3.81 (s, 2H), 3.91 (s, 2H), 7.09 (d, 2H, J=6.1 Hz), 7.13 (m, 1H), 7.29 (d, 2H, J=6.1 Hz), 7.32 (m, 1H) 7.64 (t, 1H, J=5.8 Hz), 8.54 (d, 1H, J=5.4 Hz).

The white foam was then converted to the corresponding hydrobromide salt to give AMD8922 (42 mg). $^1$H NMR (D$_2$O) δ 1.73 (m, 4H), 2.00 (m, 5H), 2.65 (d, 2H, J=7.2 Hz); 3.04–3.19 (m, 8H), 3.51 (br s, 4H), 4.38 (s, 2H), 4.58 (s, 2H), 7.32 (d, 2H, J=7.5 Hz), 7.43 (d, 2H, J=7.5 Hz), 7.85 (t, 1H, J=6.9 Hz), 7.89 (d, 1H, J=8.4 Hz), 8.34 (d, 1H, J=7.5 Hz), 8.74 (d, 1H, J=5.1 Hz). $^{13}$C NMR (CDCl$_3$) δ 24.01, 26.30, 34.51, 39.35, 41.88, 44.74, 47.47, 51.58, 69.66, 127.05, 127.16, 128.44, 130.47 (2C), 130.72 (2C), 141.74, 144.62, 146.00, 147.25. ES-MS m/z 411 (M+H); Anal. Calcd. for (C$_{25}$H$_{38}$N$_4$O×4.0 HBr×3.5 H$_2$O): C,37.66; H, 6.19; N, 7.03; Br 40.09. Found: C, 37.67; H, 6.06; N, 6.92; Br, 40.24.

EXAMPLE 5

Preparation of N-[4-(11-oxa-1,7-diazacyclotetradecanyl)-1,4-phenylenebis(methylene)]-2-(aminomethyl)pyridine (hydrobromide salt). (AMD8779, FIG. 5)

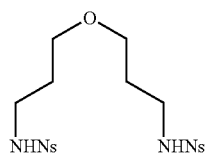

To a solution of bis(3-aminopropyl)ether (513 mg, 3.88 mmol) and triethylamine (1.7 ml, 11.78 mmol) in CH$_2$Cl$_2$ (15 ml) was added 2-nitrobenzenesulfonylchloride (97% pure, 1.95 g, 8.53 mmol) in CH$_2$Cl$_2$ (5 ml). Standard work-up followed by purification of the crude product by flash column chromatography on silica gel (10:90 EtOAc/CH$_2$Cl$_2$), gave the desired product (1.80 g, 92%) as a yellow oil. $^1$H NMR (CDCl$_3$, 300 MHz) δ 1.79–1.87 (tt, J=6.0, 6.0 Hz, 4 H), 3.20–3.26 (dt, J=6.0, 6.0 Hz, 4 H), 3.49–3.53 (t, J=6.0 Hz, 4 H), 5.75–5.79 (t, J=6.0 Hz, 2 H), 7.29–7.76 (m, 4 H), 7.86–7.88 (m, 2 H), 8.13–8.16 (m, 2 H).

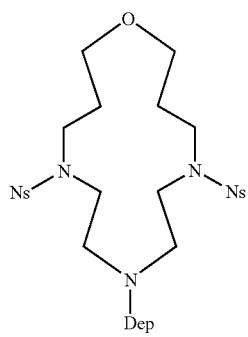

The desired macrocycle was prepared using standard macrocyclization conditions; Bridger et al. J. Med. Chem. 1995, 38, 366–378): To a stirred solution of the intermediate from above (1.8 g, 3.59 mmol) in DMF (180 ml) containing anhydrous Cs$_2$CO$_3$ (3.6 g, 11.05 mmol) heated to 80° C. was added dropwise, a solution of N-(diethoxyphosphoryl)-O,O'-bis(2-methylsulfonyl)diethanolamine (Bridger et al. J. Med. Chem. 1995, 38, 366–378) (1.9 g, 4.78 mmol) in DMF (20 ml). Evaporation of the solvent and purification of the residue by column chromatography on silica gel (30:70 ethyl acetate/CH$_2$Cl$_2$) gave the desired macrocycle (1.25 g, 55%) as a light yellow foam. $^1$H NMR (CDCl$_3$, 300 MHz) δ 1.25–1.35 (m, 6 H), 1.87–1.91 (m, 4 H), 3.05–3.14 (m, 4 H), 3.41–3.48 (m, 12 H), 3.96–4.07 (m, 4 H), 7.61–7.63 (m, 2 H), 7.68–7.71 (m, 4 H), 8.05–8.09 (m, 2 H); $^{13}$C (CDCl$_3$, 75.5 MHz) δ 16.51, 16.60, 30.63, 44.68, 44.74, 44.92, 47.24, 63.07, 63.14, 67.69, 124.52, 131.34, 132.26, 133.58, 134.11 148.32; exact mass m/z calcd. for C$_{26}$H$_{38}$N$_5$O$_{12}$PS$_2$ 707.17. found [M+H]$^+$708.5.

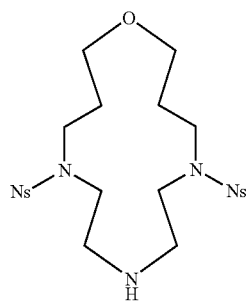

A saturated solution of anhydrous hydrogen bromide (gas) in acetic acid (8 mL) was added to the macrocycle from above (1.25 g, 1.77 mmol) contained in round bottomed flask closed by glass stopper. The resulting solution was allowed to stir overnight at room temperature and 50 ml of diethyl ether was added. The white precipitate which formed was allowed to settle to the bottom of the flask and the supernatant solution was decanted off. This white solid (HBr salt) was dissolved in 30 ml methanol and stirred with excess K$_2$CO$_3$ for 30 min and then concentrated. The residue was diluted with 300 ml ethyl acetate and the solids were filtered off by passing though a short celite column. Evaporation of the solvent and purification of the residue by column chromatography on silica gel (3:3:94 Methanol/NH$_4$OH/CH$_2$Cl$_2$) gave the desired intermediate (736 mg, 74%) as a light yellow oil. $^1$H NMR (CDCl$_3$, 300 MHz) δ 1.87–1.91 (b, 4 H), 2.85–2.88 (b, 4 H), 3.39–3.91 (t, J=6.0 Hz, 4 H), 3.49–3.56 (m, 8 H), 7.59–7.70 (m, 6 H), 7.98–8.01 (m, 2 H); $^{13}$C (CDCl$_3$, 75.5 MHz) δ 29.61, 47.90, 48.71, 68.36, 124.37, 131.07, 132.17, 133.45, 133.77, 148.65; exact mass m/z calcd. for C$_{22}$H$_{29}$N$_5$O$_9$S$_2$ 571.14. found [M+H]$^+$572.20.

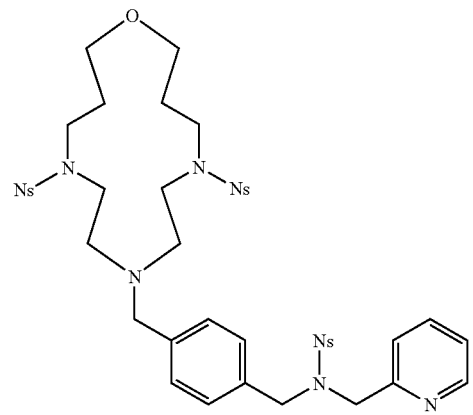

Reaction of the intermediate from above (736 mg, 1.29 mmol) with N-[1-methylene-4-(chloromethylene)phenylene]-N-(2-nitrobenzenesulfonyl)-2-(aminomethyl)pyridine (Bridger et al. U.S. Ser. No. 09/111,895) (980 mg, 2.27 mmol) and K$_2$CO$_3$ (560 mg, 4.06 mmol) in CH$_3$CN (13 mL) followed by purification of the crude intermediate by column chromatography on silica gel (10:90 ethyl acetate/CH$_2$Cl$_2$) gave desired intermediate (799 mg, 64%) as a light yellow foam. $^1$H NMR (CDCl$_3$, 300 MHz) δ 1.80–1.84 (b, 4 H), 2.58–2.62 (t, J=7.1 Hz, 4 H), 3.38–3.42 (m, 8 H), 3.50–3.55 (m, 6 H), 4.59 (b, 4 H), 7.06 (b, 4 H), 7.11–7.15 (m, 1 H), 7.18–7.21 (d, J=7.8 Hz, 1 H), 7.54–7.70 (m, 10 H), 7.87–7.89 (d, J=7.8 Hz, 2 H), 7.99–8.01 (d, J=7.8 Hz, 1 H), 8.41 (d, 1 H); $^{13}$C (CDCl$_3$, 75.5 MHz) δ 29.93, 44.77, 46.17, 51.28, 52.00, 52.30, 59.46, 67.21, 122.57, 124.11, 128.46, 128.82, 130.48, 131.06, 131.71, 133.38, 133.53, 133.61, 134.07, 136.67, 138.20, 147.93, 149.26, 155.62; exact mass m/z calcd. for C$_{42}$H$_{46}$N$_8$O$_{13}$S$_3$ 966.23. found [M+H]$^+$ 967.20.

AMD8779: N-[4-(11-oxa-1,7-diazacyclotetradecanyl)-1,4-phenylenebis(methylene)]-2-(aminomethyl)pyridine (hydrobromide salt).

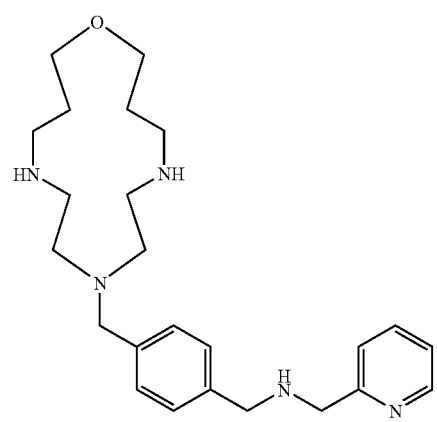

The intermediate from above (780 mg, 0.81 mmol) was reacted with anhydrous K$_2$CO$_3$ (1.36 g, 9.86 mmol) and thiophenol (644 mg, 5.84 mmol) in anhydrous DMF (8 ml). Purification of the crude material on a chromatron over silica gel (2 mm plate), using 3:3:94 CH$_3$OH/NH$_4$OH/CH$_2$Cl$_2$ gave the free amine (170 mg, 51%) as a light yellow oil. This free amine was re-dissolved in acetic acid (5 ml) saturated with anhydrous hydrogen bromide (gas), the resulting solution was allowed to stir for 30 min. at room temperature and then 50 ml of diethyl ether was added. The white precipitate which formed was allowed to settle to the bottom of the flask and the supernatant solution was decanted off. The white solid was washed by decantation with diethyl ether (5 times), and the remaining traces of solvent were removed by blowing nitrogen though the flask followed by drying in vacuo overnight at 50° C. to give AMD8779 (140 mg, 46%) as a white solid. $^1$H NMR (D$_2$O, 300 MHz) δ 1.99–2.03 (b, 4 H), 2.85–2.88 (b, 4 H), 3.25–3.29 (b, 8 H), 3.73–3.76 (t, J=5.3 Hz, 4 H), 3.82 (s, 2 H), 4.41 (s, 2 H), 4.55 (s, 2 H), 7.39–7.41 (d, J=8.1 Hz, 2 H), 7.52–7.55 (d, J=8.1 Hz, 2 H), 7.76–7.79 (m, 2 H), 8.22–8.24 (m, 1 H), 8.6–8.70 (m, 1 H); $^{13}$C (D$_2$O, 75.5 MHz) δ 6 25.58, 44.74, 46.92, 49.16, 49.98, 51.33, 55.08, 70.39, 126.57, 130.48, 130.95, 131.41, 137.27, 143.11, 147.01, 147.92; exact mass m/z calcd. for C$_{24}$H$_{37}$N$_5$O 411.30. found [M+H]$^+$ 412.30; Anal. (C$_{24}$H$_{37}$N$_5$O.4.1 HBr.4.1 H$_2$O) C, 35.28; H, 6.08; N, 8.57; Br, 40.09. Found C, 35.42; H, 6.07; N, 8.50; Br, 39.92.

EXAMPLE 6

Preparation of N-[4-(11-thia-1,7-diazacyclotetradecanyl)-1,4-phenylenebis(methylene)]-2-(aminomethyl)pyridine (hydrobromide salt). (AMD8834, FIG. 6)

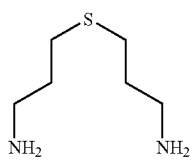

Reaction of 3,3'-thiodipropionitrile (1.81 g, 12.91 mmol) in THF (10 ml) with BH$_3$/Me$_2$S (10 M, 4.5 ml, 45 mmol) followed by work-up with 6 N hydrochloride acid (30 ml) followed by 10 N NaOH (18 ml) and evaporation of the solvent gave the crude diamine (1.4 g, 73%). $^1$H NMR (CDCl$_3$, 300 MHz) δ 1.18–1.26 (m, 4 H), 1.68–1.79 (m, 4 H), 2.55–2.60 (t, J=7.5 Hz, 4 H), 2.77–2.81 (t, J=6.0 Hz, 4 H). This material was used without further purification in the next step.

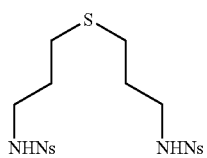

Reaction of the diamine from above (1.41 g, 9.51 mmol) with 2-nitrobenzenesulfonylchloride (97% pure, 4.7 g, 20.57 mmol) in CH$_2$Cl$_2$ (40 ml) containing triethylamine (4.2 ml, 29.01 mmol) followed by purification of the crude material by column chromatography on silica gel (10:90 EtOAc/CH$_2$Cl$_2$,) gave the desired nosyl derivative (4.5 g, 91%) as a yellow oil. $^1$H NMR (CDCl$_3$, 300 MHz) δ 1.78–1.87 (tt, J=6.8, 6.8 Hz, 4 H), 2.52–2.57 (t, J=7.5 Hz, 4 H), 3.18–3.25 (dt, J=6.0, 6.0 Hz, 4 H), 5.45–5.49 (t, J=6.0 Hz, 2 H), 7.75–7.78 (m, 4 H), 7.78–7.86 (m, 2 H), 8.13–8.16 (m, 2 H).

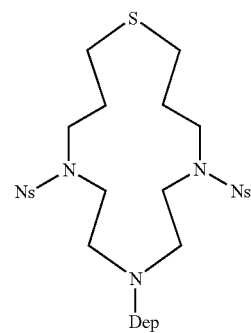

Macrocyclization was performed as described in Example 5: A solution of the intermediate from above (2.6 g, 5.01 mmol) and anhydrous Cs$_2$CO$_3$ (4.9 g, 15.04 mmol) in DMF (250 ml) was reacted with the requisite dimesylate (2.4 g, 6.04 mmol) in DMF (20 ml). Evaporation of the solvent and purification of the crude product by column chromatography on silica gel (30:70 ethyl acetate/hexanes) gave the desired macrocycle (810 mg, 23%) as a yellow foam. $^1$H NMR (CDCl$_3$, 300 MHz) δ 1.11–1.33 (m, 6 H), 1.92–1.97 (m, 4 H), 2.61–2.65 (t, J=6.0 Hz, 4 H), 3.20–3.25 (m, 4 H), 3.40–3.50 (m, 8 H), 3.97–4.05 (m, 4 H), 7.63–7.73 (m, 6 H), 8.05–8.09 (m, 2 H).

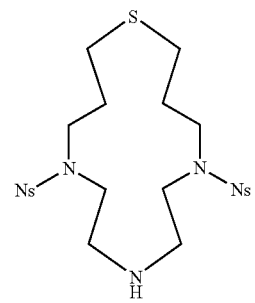

The intermediate from above (810 mg, 1.12 mmol) was dissolved in a saturated solution of anhydrous hydrogen bromide (gas) in acetic acid (10 mL). Evaporation of the solvent gave the crude amine (596 mg, 91%). $^1$H NMR (CDCl$_3$, 300 MHz) δ 1.96–2.05 (m, 4 H), 2.60–2.65 (t, J=7.5 Hz, 4 H), 2.89–2.93 (t, J=6.0 Hz, 4 H), 3.35–3.38 (t, J=4.5 Hz, 4 H), 3.42–3.46 (t, J=6.0 Hz, 4 H), 7.63–7.73 (m, 6 H), 7.96–7.99 (m, 2 H). This material was used directly in the next step.

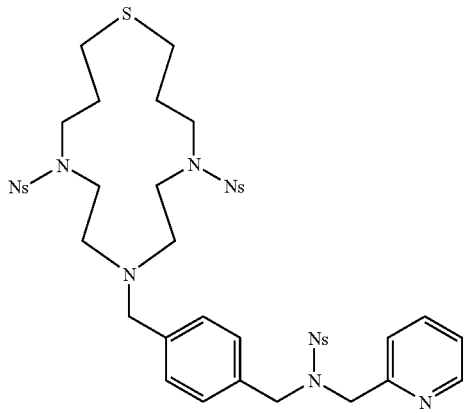

The amine from above (596 mg, 1.01 mmol) was reacted with N-[1-methylene-4-(chloromethylene)phenylene]-N-(2-nitrobenzenesulfonyl)-2-(aminomethyl)pyridine (Bridger et al. U.S. Ser. No. 09/111,895) (770 mg, 1.78 mmol) and $K_2CO_3$ (500 mg, 3.62 mmol) in $CH_3CN$ (12 mL). Purification of the crude material by chromatography on silica gel (10:90 ethyl acetate/$CH_2Cl_2$) gave the desired intermediate (400 mg, 40%) as a light yellow oil. $^1H$ NMR ($CDCl_3$, 300 MHz) δ 1.94–2.05 (m, 4 H), 2.58–2.62 (t, J=6.0 Hz, 4 H), 2.68–2.73 (t, J=7.5 Hz, 4 H), 3.31–3.36 (t, J=7.5 Hz, 4 H), 3.43–3.48 (t, J=7.5 Hz, 4 H), 3.56 (s, 2 H), 4.60 (s, 2 H), 4.75 (s, 2 H), 7.10–7.20 (m, 7 H), 7.58–7.71 (m, 9 H), 7.82 (d, 2 H), 8.0 (d, 1 H), 8.45 (d, 1 H).

AMD8834: N-[4-(11-thia-1,7-diazacyclotetradecanyl)-1,4-phenylenebis(methylene)]-2-(aminomethyl)pyridine (hydrobromide salt).

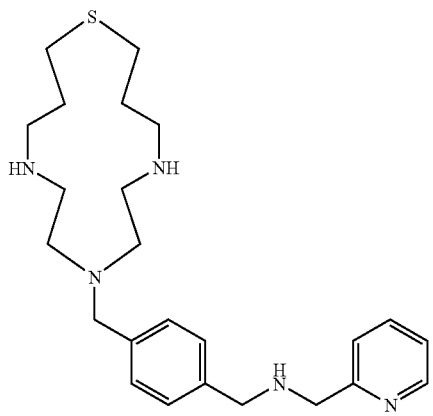

The intermediate from above (400 mg, 0.41 mmol) was reacted with anhydrous $K_2CO_3$ (674 g, 4.88 mmol) and thiophenol (322 mg, 2.92 mmol) in anhydrous DMF (8 ml). Purification of the crude product by flash chromatography on a chromatron over silica gel (2 mm plate), using 3:3:94 $CH_3OH/NH_4OH/CH_2Cl_2$ gave the free amine (107 mg, 61%) as a light yellow oil. This free amine was re-dissolved in acetic acid saturated with anhydrous hydrogen bromide (5 ml) and the resulting solution was allowed to stir for 30 min. at room temperature and 50 ml of diethyl ether was then added. The white precipitate which formed was allowed to settle to the bottom of the flask and the supernatant solution was decanted off. The solid was washed by decantation with diethyl ether (5 times) and the remaining traces of solvent were removed by blowing nitrogen though the flask followed drying in vacuo at 50° C. to give AMD8834 (196 mg, 89%) as a white solid. $^1H$ NMR ($D_2O$, 300 MHz) δ 2.03–2.07 (m, 4 H), 2.88 (m, 8 H), 3.29–3.32 (m, 4 H), 3.35–3.39 (t, J=6.2 Hz, 4 H), 3.80 (s, 2 H), 4.43 (s, 2 H), 4.61–4.62 (d, J=3.0 Hz, 2 H), 7.45–7.48 (d, J=7.8 Hz, 2 H), 7.52–7.55 (d, J=7.8 Hz, 2 H), 7.84–7.95 (m, 2 H), 8.34–8.42 (m, 1 H), 8.75 (m, 1 H); $^{13}C$ ($D_2O$, 75.5 MHz) δ 24.30, 30.12, 45.09, 47.92, 48.41, 50.27, 51.55, 55.48, 127.27, 127.42, 130.33, 130.99, 131.60, 137.59, 145.10, 145.76, 146.96; exact mass m/z calcd. for $C_{24}H_{37}N_5S$ 427.28. found [M+H]$^+$ 428.30; Anal. ($C_{24}H_{37}N_5S$) 4.3 HBr 2.6 $H_2O$) C, 35.05; H, 5.70; N, 8.52; S, 3.90; Br, 41.78. Found C, 35.18; H, 5.52; N, 8.48; S, 3.89; Br, 41.53.

EXAMPLE 7

Preparation of N-[4-(11-sulfoxo-1,7-diazacyclotetradecanyl)-1,4-phenylenebis(methylene)]-2-(aminomethyl)pyridine. (AMD9424, FIG. 7)

A solution of Oxone® (504 mg, 0.82 mmol) in water (15 mL) was added dropwise to a cooled (−10° C.) stirred solution of N-[4-(11-thia-1,7-diazacyclotetradecanyl)-1,4-phenylenebis(methylene)]-2-(aminomethyl)pyridine (350 mg, 0.82 mmol) in methanol (15 mL). The mixture was stirred at −10° C. for 10 min then poured into saturated $NaHCO_3$ solution (40 mL) and extracted with $CHCl_3$ (4×50 mL). The separated organic layers were dried ($MgSO_4$) and concentrated in vacuo. Purification of the crude product by chromatography on silica gel (3% MeOH/$CH_2Cl_2$) gave AMD9424 (75 mg, 21%). $^1H$ NMR ($CDCl_3$, 300 MHz) δ 1.90–2.01 (m, 2H), 2.06–2.17 (m, 2H), 2.59–2.85 (m, 14H), 3.07–3.18 (m, 2H), 3.57 (s, 2H), 3.83 (s, 2H), 3.92 (s, 2H), 7.17 (dd, J=7.5, 4.7 Hz, 2H), 7.23 (d, J=7.7 Hz, 2H), 7.32 (d, J=7.7 Hz, 2H), 7.65 (td, J=7.5, 1.7 Hz, 1H), 8.56 (d, J=4.9 Hz, 1H); $^{13}C$ ($CDCl_3$, 75.5 MHz) δ 24.36 (2), 47.52 (2), 48.30 (2), 52.38 (2), 52.81 (2), 53.55, 54.87, 59.11, 122.35, 122.73, 128.67 (2), 129.23 (2), 136.85, 138.00, 139.43, 149.68, 160.07; exact mass calculated for $C_{24}H_{37}N_5OS$: 443. found: m/z 444 [M+H]$^+$; Anal calculated for ($C_{24}H_{37}N_5OS.0.6C_4H_{10}O.0.4H_2O$): C, 64.02; H, 8.91, N, 14.14. found: C, 64.06, H, 8.72, N, 13.98.

EXAMPLE 8

Preparation of N-[4-(11-sulfono-1,7-diazacyclotetradecanyl)-1,4-phenylenebis(methylene)]-2-(aminomethyl)pyridine (hydrobromide salt). (AMD9408, FIG. 8)

Di-tert-butyldicarbonate (278 mg, 1.3 mmol) was added to a solution of N-[4-(11-thia-1,7-diazacyclotetradecanyl)-1,4-phenylenebis(methylene)]-2-(aminomethyl)pyridine (136 mg, 0.32 mmol) in THF (3.5 mL) and $H_2O$ (0.1 mL) and the mixture was stirred at room temperature overnight, under a nitrogen atmosphere. The mixture was concentrated and the residue was partitioned between $CH_2Cl_2$ (20 mL) and $H_2O$ (10 mL). The separated organic layer was washed with $H_2O$ (3×10 mL) and saturated NaCl solution (10 mL), dried ($MgSO_4$), and concentrated in vacuo. Flash chromatography on silica gel (3% MeOH$CH_2Cl_2$) provided the desired BOC intermediate as a clear oil (240 mg, 100%). $^1H$ NMR ($CDCl_3$, 300 MHz) δ 1.31–1.58 (m, 27H), 1.82–1.91 (m, 4H), 2.58–2.80 (m, 8H), 3.29–3.44 (m, 8H), 3.62 (s, 2H), 4.43 (s, 2H), 4.51 (d, J=7.4 Hz, 2H), 7.12–7.23 (m, 6H), 7.65 (t, J=7.5, 1H), 8.54 (d, J=4.0 Hz, 1H).

A solution of Oxone® (197 mg, 0.32 mmol) in water (2 mL) was added dropwise to a cooled (−10° C.) stirred solution of the BOC intermediate from above (232 mg, 0.32 mmol) in methanol (2 mL). The mixture was stirred at −10° C. for 10 min then poured into saturated $NaHCO_3$ solution (5 mL) and extracted with $CHCl_3$ (4×10 mL). The separated organic layers were dried ($MgSO_4$) and concentrated in vacuo to give a clear viscous oil. The crude material was purified by column chromatography on a silica gel column (3% $MeOH/CH_2Cl_2$) to give the desired sulfone (73.3 mg, 30%). $^1H$ NMR ($CDCl_3$, 300 MHz) δ 1.39–1.50 (m, 27H), 2.06–2.14 (m, 4H), 2.60–2.68 (m, 4H), 3.10 (t, J=7.2 Hz, 4H), 3.29–3.44 (m, 8H), 3.62 (s, 2H), 4.43 (s, 2H), 4.52 (d, J=4.8 Hz, 2H), 7.15–7.21 (m, 6H), 7.65 (t, J=7.5, 1H), 8.54 (d, J=4.4 Hz, 1H); exact mass calculated for $C_{39}H_{61}N_5O_8S$: 759. found: m/z 760 $[M+H]^+$.

The sulfone (73 mg, 0.96 mmol) was dissolved in a minimum amount of acetic acid and treated with a saturated solution of HBr in acetic acid (5 mL). The mixture was stirred under nitrogen for 63 h at room temperature and diethyl ether (100 mL) was added. A precipitate formed and was allowed to settle to the bottom of the flask and the supernatant solution was decanted. The white solid was washed with diethyl ether (5×100 mL) and the remaining traces of solvent were removed by blowing nitrogen though the flask followed by drying under vacuum overnight at 55° C. to give AMD9408 (70 mg, 84%) as a white solid. $^1H$ NMR ($CDCl_3$, 300 MHz) δ 2.36–2.44 (m, 4H), 2.84–2.87 (m, 4H), 3.21–3.23 (m, 4H), 3.38 (t, J=5.4 Hz, 4H), 3.67–3.70 (m, 4H), 3.73 (s, 2H), 4.34 (s, 2H), 4.39 (s, 2H), 7.44–7.51 (m, 6H), 7.93 (td, J=7.8, 1.7 Hz, 1H), 8.58 (d, J=6.1 Hz, 1H); $^{13}C$ ($CDCl_3$, 75.5 MHz) δ 18.76 (2), 45.41 (2), 47.04 (2), 47.79, 50.57 (2), 51.83, 51.88 (2), 56.71, 127.90, 128.23, 130.07, 131.03 (2), 131.29 (2), 138.44, 144.62, 145.95, 146.77; exact mass calculated for $C_{24}H_{37}N_5OS$: 459. found: m/z 460 $[M+H]^+$; Anal calculated for ($C_{24}H_{37}N_5O_2S.4$ HBr.3 $H_2O$): C, 33.14; H, 5.49, N, 8.05, Br, 40.42. found: C, 33.36, H, 5.39, N, 7.70, Br, 40.25.

EXAMPLE 9

N-[4-(3-carboxo-1,4,7-triazacyclotetradecanyl)-1,4-phenylenebis(methylene)]-2-(aminomethyl)pyridine Procedures as used in the preceding examples were used to synthesize this compound. The structure of this compound in provided in FIG. 9.

EXAMPLE 10

Inhibition of chemokine Induced Ca flux measured on a FLIPR (Molecular Devices)

Reagents:
Loading dye: Fluo-3, AM (Molecular Probes F-1241) is dissolved in anhydrous DMSO and stored frozen in aliquots. To increase the solubility of the dye in the loading medium, 10% (w/v) pluronic acid (Molecular Probes F-127) is added to the Fluo-3 stock solution immediately before use.

Flux Buffer:
HBSS+20 mM Hepes buffer+0.2% BSA, pH 7.4. HBSS 10×[(w/o phenol red and sodium bicarbonate (Gibco 14 065-049)]; Hepes buffer 1M (Gibco 15 630-056), BSA (Sigma A3675). The flux buffer is vacuum-filtered and stored refrigerated for a maximum of 5 days. Before use in the experiment, the buffer is warmed at 37° C. in a water-bath.

Antagonists:
The test compounds are diluted in flux buffer and added to 4 wells of a black microplate (4 parallel measurements per compound). The following control wells are used: 100% response control (no inhibition), flux buffer is added; 100% inhibition control: chemokine is added at 5-times the concentration required to induce a Ca flux.

Preparation of the Agonist (Chemokine) Plate:
The chemokines are diluted in flux buffer to concentrations that are 4-fold higher than the desired concentrations required for stimulation of the cells (i.e. 2.5 nM for SDF-1α). The chemokines were added to untreated 96-well Sero well compound plates (International Medical, Sterilin code 611F96). In the negative control well's (baseline monitoring), flux buffer is added instead of chemokine. As a positive control to check for dye loading efficiency, 20 μM digitonin (final concentration) is also included. The agonist plate is incubated in the FLIPR (37° C.) for 15–30 min.

Cell Loading Protocol for Measuring Inhibition of SDF-1α Induced Ca Flux in SUP-T1 Cells.
SUP-T1 cells are centrifuged at room temperature (RT) and re-suspended in loading medium (RPMI-1640 containing 2% FBS and 4 μM Fluo-3, AM). The cells are incubate at room temperature for 45 min. then washed twice in flux buffer then incubated in flux buffer at room temperature for 10 min. The cells are centrifuged and re-suspended in flux buffer at a density of 3×10$^6$ cells per mL. A 100 μL aliquot of the cell suspension (3×10$^5$ cells) is added to each well of a black microplate (Costar 3603), which already contains 50 μL of a solution of the test compound (at concentrations that are 3-fold higher than the desired final compound concentrations). The microplate is then gently centrifuged at room temperature. Homogeneous spreading of the cells on the bottom of the microplate wells is then confirmed with a microscope and the microplate was incubated in the FLIPR (37° C.) for 10 min. prior to testing.

Fluorescence Measurements as a Function of Time on the FLIPR
The FLIPR settings (camera exposure time and laser power) are adjusted to obtain initial fluorescence values between 8,000 and 10,000 units. After monitoring a 20 second-baseline, the agonist (chemokine) (50 μL) is added by automatic pipettor with black pipette tips. Fluorescence is measured simultaneously in all wells of the microplate every 2 seconds (first 2 min) and thereafter every 6 seconds (additional 2 min). The average ca-flux measured in each set of 4 identical wells (one test compound) was calculated by the FLIPR software.

The compounds of the current invention were tested for inhibition of SDF-1α induced Ca flux in SUP-T1 cells using the method described above. The compounds described in Examples 1–9 inhibited SDF-1α induced Ca flux greater than 50% at 25 μg/mL.

EXAMPLE 11

Assay for Inhibition of HIV-1 (NL4.3) Replication in MT-4 Cells

Inhibition of HIV-1 NL4.3 (or III$_B$) replication assays were performed as previously described (Bridger, et al., *J. Med. Chem.* 42:3971–3981 (1999); De Clercq, et al., *Proc. Natl. Acad. Sci.* 89:5286–5290 (1992); De Clercq, et al., *Antimicrob. Agents Chemother.* 38:668–674 (1994); Bridger, et al. *J. Med. Chem.* 38:366–378 (1995)). Anti-HIV activity and cytotoxicity measurements were carried out in parallel. They were based on the viability of MT-4 cells that had been infected with HIV in the presence of various concentrations of the test compounds. After the MT-4 cells were allowed to proliferate for 5 days, the number of viable cells was quantified by a tetrazolium-based colorimetric 3-(4,5-dimethylthiazol-2-yl)-2,5-diphenyltetrazolium bromide (MTT) procedure in 96-well microtrays. In all of these assays, viral input (viral multiplicity of infection, MOI) was 0.01, or 100 times the 50% cell culture infective dose ($CCID_{50}$). The $EC_{50}$ was defined as the concentration required to protect 50% of the virus-infected cells against viral cytopathicity.

The compounds of the current invention were tested as described above. The compounds described in Examples 1–9 inhibited HIV-1 replication with $EC_{50}$'s in the range 0.003–33.3 ug/mL.

EXAMPLE 12

Inhibition of Collagen-Induced Arthritis

A compound related to those of the invention demonstrated inhibition of collagen-induced arthritis (CIA) in a mutant mouse model.

Experimental Animal Treatment

The control group consisted of ten mice that were injected with collagen as discussed below. The treatment group consisted of eight mice which were also injected with collagen and were further treated by administering 1,1'-[1,4-phenylenebis(methylene))]bis-1,4,8,11-tetraazacyclotetradecane (AMD 3100; see FIG. 10) intravenously using osmotic pumps (200 µl, Alza, 0.5 µl/hr) at a concentration of 5 mg/ml over a 14-day period following collagen injection.

Mutant Mice

The generation and the basic characteristics of the mutant mouse strain (129/Sv/Ev) with a disruption in the gene coding for the α-chain of the IFN-γ receptor (IFN-γ RKO) have been described (Huang, S., et al., Science 259:1742 (1993)). These IFN-γ RKO mice were back-crossed with DBA/1 wild-type mice for 10 generations to obtain the DBA/1 IFN-γ RKO mice used in the present study. IFN-γ RKO and wild-type mice were bred in the Experimental Animal Centre of the University of Leuven. The experiments were performed in 8- to 12-week old mice, but in each experiment, the mutant and wild-type mice were age-matched with a 5 day limit. The male to female ratio was kept between 0.8 and 1.3 in each experimental group.

Induction of Collagen-Induced Arthritis and Clinical Assessment of Arthritis

Collagen-induced arthritis was carried out in the following manner (see: Vermeire, et al., Int. J. Immunol. 158: 5507–5513, (1997)). Native chicken collagen type II (EPC, Owensvillle, Mo.) was dissolved in 0.05 M acetic acid at 2 mg/ml by stirring overnight at 6° C., and emulsified in an equal volume of incomplete (IFA) or complete Freund's adjuvant (CFA) containing 1.5 mg/ml heat killed *Mycobacterium butyricum* (Difco, Detroit, Mich.). Mice were sensitized with a single 100 µl intradermal injection of the emulsion at the base of the tail. Mice were examined daily for signs of arthritis. The disease severity was recorded following a scoring system for each limb. Score 0: normal; score 1: redness and/or swelling in one joint; score 2: redness and/or swelling in more than one joint; score 3: redness and/or welling in the entire paw; score 4: deformity and/or ankylosis.

Histological Examination

Spleens and fore and hind limbs were fixed in buffered saline-B5fixative (10% formalin with quicksilver). Alternatively, tissues were fixed in 10% formalin or pure methanol (see: Vermeire, et al., J. Immunol. 158:5507–5513 (1997)). Limbs were subsequently decalcified overnight with formic acid. Four-micron thick paraffin sections were stained with hematoxylin and eosin. Severity of arthritis was evaluated using three parameters: infiltration of mono- and polymorphonuclear cells, hyperplasia of the synovium and parmus formation. Each parameter was scored on a scale from 0 to 3 (absent; weak, moderate and severe).

In Vivo Antibody Treatments

Monoclonal antibodies were produced from hybridomas grown by intraperitoneal inoculation in Pristane-primed athymic nude mice (nu/nu of NMRI background). Neutralizing monoclonal antibody against MuIFN-γ (F3, rate $IgG_{24}$) was purified by affinity chromatography on a mouse anti-rat κ chain monoclonal antibody (Billiau, A., et al., J. Immunol. 140:1506 (1988)). The neutralizing titer (end-point dilution corresponding to 50% neutralization of the antiviral effect of 30 units/ml of mouse IFN-γ on mouse I929 cells challenged with mengovirus) was $10^{5.3}$ U/ml (IgG content, 1.4 mg/ml). A neutralizing rate $IgG_{24}$ antibody against murine IL-12 was produced using hybridoma C17.8 (kindly provided by Dr. G. Trinchieri, Wistar Institute, Philadelphia, Pa.). The antibody was purified by affinity chromatography on protein G (Pharmacia, Uppsala, Sweden). Antibody against murine IL-6 was prepared from ascites fluid from thymus-less nude mice inoculated with the 20F3 (rat×mouse) hybridoma (American Type Culture Collection, Rockville, Md.). This rat IgG antibody was purified by affinity chromatography on an anti-rat κ chain monoclonal antibody-Sepharose column. The neutralizing titer (endpoint dilution corresponding to 50% neutralization of the cell growth effect of 10 U of murine IL-6 per ml) was $10^{5.5}$ (IgG content: 2.9 mg/ml). Irrelevant rat $IgG_{24}$ was used as an isotype control and was prepared from ascites fluid of a rat plasmocytoma (obtained through the courtesy of Dr. H. Bazin, University of Louvain, Medical School, Brussels, Belgium). The IgG was purified by anion exchange chromatography on Hiload Q Sepharose and gel filtration on Superdex 200 (Pharmacia). Batches of anti-IFN-γ, anti-IL-12, anti-IL-6 and irrelevant $IgG_{24}$ were tested for endotoxin content by a chromogenic Limulus amoebocyte lysate assay (KabiVitrum, Stockholm, Sweden) and were found to contain less than 2 ng/ml endotoxin. Injections were given in 200 µl of pyrogen-free saline.

Following 14 days after treatment, 7 of the ten mice in the control group demonstrated arthritis, while only 1 of the 8 animals treated with AMD 3100 demonstrated disease. The single treated animal did not develop arthritic pathology until after 20 days post-treatment. Additionally, the treated animals compared with the control animals did not demonstrate any significant body weight loss. Further, the treated animals maintained body weight consist with healthy animals not injected with collagen.

EXAMPLE 13

Treatment of Glioblastoma

Compounds of the present invention may be used in the treatment of glioblastomas, fibromas, astrocytomas or myelomas affecting the central nervous system. The compounds may be used according to standard clinical practice and procedures, using dosages as provided in the foregoing examples and according to clinical end points, such as imaging, immunological and other methodologies.

For example, the etiology or association of chemokine receptor binding in the proliferation of glioblastoma tumor cells has been reported by Sehgal, et al., *J. of Surg. Oncolo.* 69:99–104 (1998) ("Sehgal I") and Sehgal, et al., *J. of Surg. Oncolo.* 69:239–248 (1998) ("Sehgal II"). The role of CXCR4 of its binding to its receptor appears to play a significant role in the formation and/or proliferation of glioblastoma cells. The inhibition of the binding by CXCR4 to its natural receptor ligand by compounds of the present invention offer a new drug in the treatment tumors of central nervous system that are mediated or associated with chemokines, such as CXCR4.

EXAMPLE 14

Treatment of Non-Small Cell Lung Cancer

Compounds of the present invention may be used in the treatment of non-small cell lung cancer. The compounds may be used according to standard clinical practice and procedures, using dosages as provided in the foregoing examples and according to clinical end points, such as imaging, immunological and other methodologies.

For example, CXC chemokines have been found to regulate or are associated with the regulation of angiogenesis in non-small cell lung cancer (see: Arenberg, et al., *J. of Leukocyte Biol.* 62:554–562 (1997); and Moore, et al., *TCM*, vol. 8(2):51–58 (1998) Elsevier Science, Inc.). The role of CXC chemokines and the binding to their respective receptors appear to play a significant role in the formation and/or proliferation of non-small cell lung cancer promoted by an increase in angiogenic activity. The inhibition of the binding of these CXC chemokines to their natural receptor ligands by compounds of the present invention offer a new drug in the treatment tumors such as non-small cell lung cancer that are mediated or associated with increased levels of chemokines.

The invention claimed is:

1. A method to treat atherosclerosis comprises comprising administering to a subject in need of such treatment a compound of the formula

$$V\text{—}CR_2\text{—}Ar^1\text{—}CR_2NR\text{—}(CR_2)_x\text{—}Ar^2$$

wherein V is a heterocycle of 9–24 members containing 2–4 optionally substituted amine nitrogen atoms spaced from each other by 2 or more optionally substituted carbon atoms, and which heterocycle may optionally comprise a fused aromatic or heteroaromatic ring, and wherein (a) said heterocycle contains at least one O or S, said O or S spaced from any adjacent heteroatom by at least 2 carbon atoms, and wherein said S is optionally oxidized, or (b) the heterocycle contains 3 N and at least one carbon atom in said heterocycle is substituted by at least one fluoro substituent, or (c) both (a) and (b);

and wherein each R is independently H or a straight chain, branched or cyclic alkyl containing 1–6C;

x is 0–4;

$Ar^1$ is an unsubstituted or substituted aromatic or heteroaromatic moiety; and $Ar^2$ is an unsubstituted or substituted aromatic or heterocyclic group; or the pharmaceutically acceptable salts and protected forms thereof.

2. The method of claim 1 wherein each R is independently H or methyl.

3. The method of claim 1 wherein x is 1.

4. The method of claim 1 wherein $Ar^1$ is 1,3 or 1,4-phenylene.

5. The method of claim 1 wherein $Ar^2$ is phenyl or pyridyl.

6. The method of claim 1 wherein V is a 12–16 membered heterocycle.

7. The method of claim 1 wherein V contains O or S as a ring member.

8. The method of claim 1 wherein x is 0–2.

9. The method of claim 1 wherein x is 1–2.

10. The method of claim 7 wherein said S is oxidized.

11. The method of claim 1 wherein at least one carbon in V is substituted by =O.

* * * * *